(12) United States Patent
Pedersen et al.

(10) Patent No.: US 7,244,273 B2
(45) Date of Patent: Jul. 17, 2007

(54) PROSTHETIC DEVICE

(75) Inventors: Walther Batsberg Pedersen, Copenhagen (DK); Frederik Resen Steenstrup, Copenhagen (DK); Ole Ingemann Olsen, Charlottenlund (DK); Lene Diness Jakobsen, Copenhagen (DK); Erik Vraa, Copenhagen (DK); Jes Bruun Lauritzen, Farum (DK); Klaus Bechgaard, Copenhagen (DK)

(73) Assignee: Cartificial A/S, Kobenhavn O (DK)

( * ) Notice: Subject to any disclaimer, the term of this patent is extended or adjusted under 35 U.S.C. 154(b) by 604 days.

(21) Appl. No.: 09/926,756

(22) PCT Filed: Dec. 14, 2000

(86) PCT No.: PCT/DK00/00697

§ 371 (c)(1),
(2), (4) Date: May 3, 2002

(87) PCT Pub. No.: WO01/45595

PCT Pub. Date: Jun. 28, 2001

(65) Prior Publication Data

US 2003/0093152 A1    May 15, 2003

(30) Foreign Application Priority Data

Dec. 17, 1999    (DK)    ............... 1999 01811

(51) Int. Cl.
*A61F 2/08* (2006.01)
*A61F 2/02* (2006.01)

(52) U.S. Cl. .................. 623/14.12; 623/23.72

(58) Field of Classification Search ............ 623/14.12, 623/16.11, 17.11, 17.15, 17.16, 13.11, 23.72–23.76
See application file for complete search history.

(56) References Cited

U.S. PATENT DOCUMENTS 4,446,578 A    5/1984    Perkins et al. ................ 3/1.91
4,502,161 A *  3/1985    Wall ........................ 623/14.12
(Continued)

FOREIGN PATENT DOCUMENTS

EP    0 339 607    11/1989
(Continued)

OTHER PUBLICATIONS

Shikinami et al.; Potential application of a triaxial three-dimensional fabric (3-DF) as an implant; Biomaterials 19, 1998, pp. 617-635.

* cited by examiner

*Primary Examiner*—Alvin J. Stewart
(74) *Attorney, Agent, or Firm*—Jacobson Holman PLLC

(57) ABSTRACT

The present invention relates to a method and a device for alleviating and/or preventing conditions relating to damaged joints involving articulating surfaces. In a first aspect the present invention relates to a prosthetic device for insertion into a joint cavity of a joint of a vertebrate, such as a human, said device consisting of a biocompatible material comprising at least a first polymeric component and a second polymeric component, wherein the chain length of the first polymeric component is longer than the chain length of the second polymeric component, the polymeric components in particular being polyethylene, polypropylene and/or polyvinylpyrrolidone. A further aspect of invention relates to a method for introducing the prosthetic device into a joint, such as a method comprising locking the device to an intro-articular component, thereby fixing or retaining the device in the joint cavity in a manner which is substantially non-invasive with respect to cartilage and bone natively present in the joint cavity. Also the invention relates to an instrument for inserting a prosthetic device according to the invention, comprising means for deforming the prosthetic device into a reduced volume or a slender shape and means for grasping the intra-articular component to which the device is capable of interlocking.

51 Claims, 10 Drawing Sheets

U.S. PATENT DOCUMENTS

| | | | |
|---|---|---|---|
| 4,919,667 A * | 4/1990 | Richmond | 623/14.12 |
| 5,067,964 A * | 11/1991 | Richmond et al. | 623/14.12 |
| 5,108,441 A | 4/1992 | McDowell | 623/19 |
| 5,258,037 A | 11/1993 | Caspers | 623/36 |
| 5,304,595 A | 4/1994 | Rhee et al. | 525/54.1 |
| 5,545,229 A | 8/1996 | Parsons et al. | |
| 5,879,396 A * | 3/1999 | Walston et al. | 623/23.41 |
| 2003/0212456 A1 * | 11/2003 | Lipchitz et al. | 623/13.17 |

FOREIGN PATENT DOCUMENTS

| | | |
|---|---|---|
| EP | 0 365 108 | 4/1990 |
| EP | 0 372 811 | 6/1990 |
| EP | 0 373 800 | 6/1990 |
| EP | 0 444 244 | 9/1991 |
| EP | 0 505 634 | 9/1992 |
| EP | 0 528 080 | 2/1993 |
| EP | 0 530 804 | 3/1993 |
| EP | 0 552 949 | 7/1993 |
| EP | 0 591 898 | 4/1994 |
| EP | 0 597 553 | 5/1994 |
| EP | 0 698 382 | 2/1996 |
| EP | 0 876 820 | 11/1998 |
| FR | 2 635 678 | 3/1990 |
| FR | 2 682 590 | 4/1993 |
| GB | 1 542 714 | 3/1979 |
| WO | 86/05984 | 10/1986 |
| WO | 89/01009 | 2/1989 |
| WO | 90/09769 | 9/1990 |
| WO | 92/10982 | 7/1992 |
| WO | 92/19183 | 11/1992 |
| WO | 93/09819 | 5/1993 |
| WO | 93/11723 | 6/1993 |
| WO | 93/25187 | 12/1993 |
| WO | 94/01483 | 1/1994 |
| WO | 94/02086 | 2/1994 | dam
PROSTHETIC DEVICE

FIELD OF INVENTION

The present invention relates to a method and a device for alleviating and/or preventing conditions relating to damaged joints involving articulating surfaces.

GENERAL BACKGROUND

At present, joint damage, such as cartilage damage, is treated by replacing the joint with an artificial joint. However, serious complications are caused by the replacement of artificial joints, in particular a high occurrence rate of loosening problems resulting in breakage of the bones around the artificial joint.

In particular, the invasive character of the fixation of the prostheses such as anchoring of the prosthesis with screws and pins results in numerous side-effects such as risk of infection, loosening as mentioned above, damage on excising bone due to interruption of blood supply and necrosis.

A device for replacement within a joint should preferably enable the normal function and movements of the joint. Weight-bearing joints, in which movement in more than one direction takes place, are normally rather difficult to replace.

A prosthetic device should enable the normal movement of the joint. During walking, the normal movement of for example the hip joint corresponds to about 37°-41° flexion/extension, 2°-14° adduction/abduction and a rotation of about 2°-16°. During movement from standing to sitting position a flexion of hip joint corresponds to a movement from 0 to 90 degrees. When studying the movement of femoral caput to the acetabulum the latter movement includes a rotation of 90 degrees.

So far, no satisfactory device for placement within a joint has been achieved in the prior art.

SUMMARY OF THE INVENTION

In a first aspect the present invention relates to a prosthetic device for insertion into a joint cavity of a joint of a vertebrate, such as a human, said device consisting of a biocompatible material comprising at least a first polymeric component and a second polymeric component, wherein the chain length of the first polymeric component is longer than the chain length of the second polymeric component.

The invention disclosed furthermore relates to a prosthetic device for insertion into a joint cavity of a joint of a vertebrate such as a human, wherein the body of the device comprises a polymer material, and wherein the device is non-invasive with regards to the intra-articular components when the device is in the joint cavity, said device being adapted to alleviate conditions associated with worn cartilage;

and in a third aspect the present invention provides:

a prosthetic device for insertion into a joint cavity of a vertebrate such as a human, wherein the body of the device comprises a polymer material, and wherein the device comprises a hole extending through the body of the device.

By the term "non-invasive" is meant that the device is preferably not attached to joint components through the use of screws, stitches or the like.

Also, the invention relates to a method for introducing a prosthetic device into a joint, such as a method comprising locking the device to an intra-articular component, thereby fixing or retaining the device in the joint cavity in a manner which is substantially non-invasive with respect to cartilage and bone natively present in the joint cavity.

Another aspect of the invention is an instrument for inserting a prosthetic device according to the invention, comprising means for deforming the prosthetic device into a reduced volume or a slender shape and means for grasping the intra-articular component to which the device is capable of interlocking.

Yet a further aspect of the invention relates to the use of a prosthetic device for establishing slidability and/or distributing pressure in a joint of a vertebrate such as a human, by inserting into the joint cavity of the joint a prosthetic device, preferably a prosthetic device as defined in this invention, capable of locking itself to an intra-articular component and thereby being fixed or retained in the joint cavity in a manner which is substantially non-invasive with respect to cartilage and bone natively present in the joint cavity.

Another aspect relates to a method for establishing slidability and/or pressure distribution in a joint of a vertebrate such as a human, comprising inserting into the joint cavity of the joint, a prosthetic device, preferably a prosthetic device as defined herein, which is capable of locking itself to an intra-articular component and thereby being fixed or retained in the joint cavity in a manner which is substantially non-invasive with respect to cartilage and bone natively present in the joint cavity.

Yet another aspect is a kit comprising:

a) an intra-articular prosthetic device for a joint having
  a.1) a spacer function and/or capability to exert pressure distribution and/or sliding/rotating movement of the joint by internal movement of the device by means of a resilient member, and
  a.2) a locking mechanism adapted to fix the device to an intra-articular component by means of an element of the device surrounding the component in such a manner that displacement of the device is limited by inter-locking with the component; and b) an instrument for inserting the prosthetic device into a joint cavity.

DETAILED DESCRIPTION OF THE INVENTION

The device and units are designed to occupy at least part of the intra-articular cavity to partly or completely fill the role of natural cartilage within a joint. The device or its units may be designed so as to occupy the whole of the cavity or merely a portion of the intra-articular cavity, such as the portion of the cavity where cartilage is worn or where much of the pressure is exerted. The device and its units may radially encircle an intra-articular component spanning a longitudinal axis of the cavity or may occupy one or more portions of the cavity laterally removed from the intra-articular component and its axis.

The device and units may be designed not to interfere and to be non-invasive with regards to intra-articular components when the device is in the joint cavity by means such as a slit in the body of the device.

Moreover, non-interference of the intra-articular components may be achieved by a hole which runs through the body of the device; that is to say the device may comprise a hole through which intra-articular components may pass. When loading the device, the slits may serve to pass intra-articular components through the body of the device.

The slits in this embodiment run from the periphery of the body of the device to the hole through which the intra-articular components pass after the device is implanted or loaded.

Typically, and to at least some extent, the device is adapted in its structure and/or material composition to alleviate conditions associated with worn cartilage by providing a spacer function and/or to exert pressure distribution in the joint when the joint is loaded and/or to provide at least part of the sliding/rotating movement of the joint by internal movement of at least part of the device.

It is also an object of the present invention to provide a method for non-invasive locking of a device within a joint. In addition, the method is independent of use of cement or bony ingrowth of the device.

A still further object of the present invention is to provide a kit for use in the method for non-invasive locking of a device within a joint.

It is also an object of the present invention to provide a method for preventing damage between mating surfaces or articulating surfaces within a joint such as between the femoral head and the acetabulum of a hip joint.

A more specific object of the present invention relates to a prosthetic device for insertion into a joint cavity of a joint of a vertebrate such as a human, the device is being adapted to provide a spacer function and/or to exert stress distribution in the joint when the joint is loaded and/or to provide at least part of the sliding/rotating movement of the joint by internal movement in the material of at least part of the device, the device being capable of locking itself to an intra-articular component and thereby being fixed or retained in the joint cavity in a manner which is substantially non-invasive with respect to cartilage and bone natively present in the joint cavity.

Physical-Structural Features of the Device

The physical-structural features of the device relate to the size, form or shape of the device as well as the structural components and design components of the device.

Size and Shape

The overall shape of the device is such that it substantially fits into the excising anatomical dimensions of the joint. In general, the size and shape of the device are such that the device fits into the intra-articular cavity in that it may partially or fully occupy the space defined by the cavity. For some of the joints it is preferred that the extent of the device, when positioned in the joint cavity, is larger than the normal extent of cartilage on the bone end in that joint.

In a preferred embodiment, a hole runs through the body of the device to allow intra-articular components to traverse the body of the device and thus be surrounded by the device.

In this embodiment, the device may be construed in a liberal sense as essentially torus-shaped in that the device can be of a plurality of geometrical shapes, symmetrical and asymmetrical, comprising a hole which runs through the body to create an internal tubular passage through which intra-articular components may pass.

The device may also be ball-shaped, disc-shaped, spherical, globular-shaped, cup-shaped, cone-shaped, ring-shaped, cylindrical and have convex, concave, or flat surfaces. Accordingly, the body of the device shape can e.g. be in the form of a horseshoe, a curl, ring-shaped, circular or semi-circular so as to be suitable for fitting into the anatomical dimensions of the particular joint. Furthermore, the device may be unsymmetrical.

The body of the device may be of a geometrical shape comprising a surface having the form of body shaped by rotating a circle about a coplanar axis which does not intersect the circle. It may be ball-shaped, disc-shaped, globular-shaped, cup-shaped, cone-shaped, ring-shaped, cylindrical and may comprise convex, concave, or flat surfaces. In some aspects it is characterised in that it comprises a hole extending from one surface of the body of the device to the same or another surface, creating an internal tubular cylinder. This internal tubular cylinder may be straight if the hole extended to two parallel surfaces, curved if the hole extends to perpendicular surface, U-shaped if the hole extends to two parts of the same surface or a combination of one or more of these internal shapes and thus tortuous.

Certainly, given that the overall shape of the device is such that it substantially fits into the excising anatomical dimensions of the joint, it is anticipated that the body of the device may be asymmetrical or of no definable shape so as the fill the intra-articular cavity, to allow for the movement of the intra-articular components during the flexing of the joint, to support intra-articular components or to support matter which form the walls of the cavity.

It is preferable that the shape of the device is such that it does not impede the normal functioning of the joint and its components.

It is particularly anticipated that the body of the device may be asymmetrical or of no definable or uniform shape when the device is for use in a hip joint. Alternatively, the shape of the device may be such that it resembles the native cartilage, or part thereof, naturally present in the joint cavity.

Accordingly, in the case of a hip joint, the shape of the device is preferably such that it fits into the existing space of the joint cavity comprising ligamentum capitis femoris, the "walls" of the space being defined by the concave shape of the acetabulum and by the convex shape of the femoral head.

Moreover, the overall shape of the device may be a result of an assembly of more than one units of the device, such as the assembly of two or more rings of different sizes stacked upon each other so as to form a cone-shaped device. The assembly of units may be done in vivo or ex-vivo.

Furthermore, in preferred embodiments, the overall shape is such that the device is capable of locking itself to an intra-articular component if present in said joint and thereby being fixed or retained in the joint cavity. When the intra-articular component is a ligament, the shape is such that the ligament is surrounded or substantially surrounded by the device.

However, the overall shape of the device may have any other form as long as the material is of such a character that the device when present in situ fits into the joint cavity, for example due to elastical deformation of the device.

Preferably, the elastical deformation of the device is such that the presence of ligamentum capitis femoris results in a shape leaving room for the ligamentum. Otherwise, the surface of the upper part of the device facing the acetabular cavity may comprise a groove embedding the ligament.

Typically, the shape of the device is formed from a moulding of its materials or from a casting process. It may alternatively be the result of a framed structural construction or skeletal assembly. It is typically solid in that the body of the device is not hollow but rather such that the material of the device comprises all or essentially all of the space between two surfaces. The moulding, casting, construction or assembly may form a device into a uniform or non-uniform shape.

The device is essentially uniform in its stiffness or compressibility. However, when loaded, the material may have a tendency to deform in such a way that the locking mechanism is altered. This may occur if the element adapted to surround the ligament, when present in situ, has a slit which expands or gapes upon loading when the device is pressed together. This gaping may be further pronounced when the patient is e.g. walking whereby the ceiling of the acetabulum is pressed down on the upper surface of the device and the lower surface of the device is pressed down on the spherical surface of the femoral head.

Due to the rolling movement (rotation within the joint) of the femoral head, the possibility exists that the femoral head may press itself up into the slit of the device during the movement. In such cases, the press distribution and/or internal movement of the device may be limited to a minor part of the device that may result in an undesirable increased pressure on that portion of the device. Finally, contact between the femoral head and the acetabulum may occur in case the femoral head penetrates through the device. However, a device comprising parts overlapping each other can prevent this possible undesirable effect.

Accordingly, as mentioned above, the device may be curl-shaped whereby the device with respect to the slit or opening has overlapping parts which do not represent a complete opening in the loading direction.

The size of the prosthetic device according to the invention may be of any size corresponding to the dimensions of the joint. In a hip joint, a suitable size is normally one that allows the diameter of the device to be about the same or less than the diameter of the femoral head. However, on some occasions the diameter may exceed that of the femoral head. The size may also depend on the degree of damage of the native cartilage of the joint. Moreover, the space available within the joint in the individual may have an effect on the preferred diameter. Also the compressibility of the material should be taken into account. In the case in which the material is highly compressible, the device may increase in diameter upon loading of the joint; when loaded, the device should generally cover the surface area which is covered with cartilage in the normal joint, e.g., in the hip joint, the surface of caput femoris should preferably be substantially covered when the joint is loaded to avoid contact of the surface of the femoral head with the acetabulum.

The length of the diameter of the device is designed to fit into the particular joint, such as between 15-80 mm, such as between 25-70 mm, preferable between 30-60 mm, more preferable between 35-50 mm, most preferred about 40 mm, when the joint is loaded.

The prosthetic device according to the invention may vary in thickness depending on the load on the joint, and the thickness of the device may also vary within the device.

The thickness of the device is at least 0.5 mm, such as at least 1.0 mm preferably between 2-60 mm, such as between 6-40 mm, preferably 8-30 mm, more preferably about 10-20 mm, most preferably about 15 mm in the unloaded stage. Depending on the material, the device may be highly compressible, whereby the initial thickness may exceed the above-mentioned upper limit. If only a limited rotation takes place in the joint, the thickness of the device may be decreased.

In one embodiment of the invention, the device is capable of locking itself to the intra-articular component by at least one element of the device surrounding the component in such a manner that displacement of the element, and thereby the device, is limited by interlocking with the component. The intra-articular component which is surrounded is preferably a ligament, such as a ligament natively existing in the joint cavity.

In one embodiment of the device according to the invention, the element completely or substantially completely surrounds the ligament.

Thus, one embodiment of a prosthetic device according to the invention relates to a device wherein the element interlocking with a ligament, when present in situ, permits the ligament to extend through the element and substantially exert its natural function on the joint.

In one aspect of the invention, the prosthetic device is intended for the articulation of a hip of a human, said device being adapted such that when present in situ in the human hip joint cavity, it comprises at least one element surrounding ligamentum capitis femoris. Accordingly, ligamentum capitis femoris represents the surrounded intra-articular element mentioned above.

It is contemplated that the surrounding of the intra-articular component by the element may be a completely or substantially completely encircling of the ligament.

It is also preferred that the prosthetic device, when present in situ, comprises at least one ring-shaped or substantially ring-shaped element.

According to another aspect of the invention, the element of the prosthetic device which is adapted to surround the ligament when present in situ has such a shape and such properties that it can be placed around the ligament and stay interlocked with the ligament.

Structural Components

The device preferably comprises structural components which permit arrangement of the body of the device around native intra-articular components.

When the prosthetic device according to the invention is a hip endoprothesis, the device has a shape and structural components permitting arrangement of the body of the device around ligamentum capitis femoris.

A prosthetic device according to the invention comprises a device wherein the element of the device interlocking with the device with an intra-articular component has such a shape and/or properties that it is capable of replacing or supplementing worn or damaged cartilage in the joint and/or is capable of preventing wear of the native cartilage of the joint or of the bone tissue of the joint.

The structure of the material of the device or of a part of the device may be in the form of fibres and filaments which can be incorporated into the matrix in a braided, woven, spongy or spiral pattern, the fibres and filaments having reinforcing properties. The fibres may be inorganic fibres such as carbide, nitride, boride, carbon and oxide fibres, or the reinforcement may be of organic origin such as Dacron™. In a preferred embodiment the fibres are selected from polyethylene fibres, polypropylene fibres or a combination thereof.

The structure of the material of the device may comprise a layered or laminated structure, a core of one material or one or more interposed layers with different properties enabling an overall function of the devise suitable for providing a spacer function and/or to exert pressure distribution in the joint when the joint is loaded and/or to provide at least part of the sliding/rotating movement of the joint by internal movement of the device, or relevant part of the device. However, it is preferred that the material itself does not comprise interposed layers resulting in sliding between the layers and thereby tear on the mating surfaces within the device. Accordingly, the body of the device should be one continuous solid or semi-solid material.

In one preferred embodiment of the invention, the device comprises a tubular passage through which the ligament can pass and be surrounded by the body of the device, as depicted in FIG. 5. Circular movement around the substantially central ligament is possible but replacement of the device is prevented. A further feature of the structure of the device may be that of a slit extending from the outer surface of the device and through the body of the device into the central tubular passage. The slit may be curl-shaped in the radial direction with the axis of the tubular passage being the centre as depicted in FIGS. 7, 9 and 11.

The slit may curl or curve into the body of the device so as to form an S-, or C-shaped slit, or zigzag or spiral slit. The curl of the slit may be in the two dimensions of a disc shaped device, as in FIG. 7, or may curl in all three dimensions in the case of a globular, spherical, cone-shaped or cup-shaped device, as depicted in FIG. 9, 19, 22, or 27.

Furthermore, in embodiments where the device comprises more than one unit, the curvature of the slit may be such as to form a zigzag, spiral or S- or C-shaped multi-unit slit.

In multi-unit devices, the outer surfaces of the parts of the unit which are in contact with each other may have a surface pattern preventing the units from sliding apart such as grooves or etching or jagged surface pattern, as depicted in FIG. 23.

Moreover, the overall shape of the device may be from an assembly of two or more elements of one device, such as two semi-circular elements assembled to form a ring or from the assembly of two elements obtainable from the cross-sectioning of a ring or globular device along their longest axis. As was the case for the surface of two units, two elements may have a surface pattern preventing the elements from sliding apart such as grooves or etching or jagged surface pattern. Thus, a device and its shape may be the result of an assembly of two or more elements and/or two or more units, each comprising surfaces designed to preventing slippage of units and/or elements, as depicted in FIGS. 26-28.

If suitable, the device may comprise a material which functions as a frame for the shape or secures the device from opening when placed in situ, for example in the form of a shaped component having the properties of a spring or the like.

In one embodiment, the ring-shaped body of the device has a slit or other suitable means which enables the device to be placed in the position encircling ligamentum capitis femoris.

Upon loading the device into the joint, the element of the device surrounding the component, e.g. a ligament, and thereby interlocking with the component, may tend to open up due to deformation of the device in the form of flattening resulting in an increased diameter. When the diameter of the device increases, e.g. the diameter of a ring-shaped device comprising a slit, the adjoining surfaces of the slit may gape.

As stated, during the compression, extension or rotation of the device when the device is present in a joint, the slit may have a tendency to gape and thus result in reduced weight-bearing effectiveness and/or result in trapping of intra-articular components within the seam of the slit. Preferably, the seam cannot be pulled apart in the direction of the plane of the seam by the mechanical pressure exerted by the body of the device conferred by the elastic properties of the material.

To prevent undesired slippage of the seam perpendicular to the plane of the seam, a variety of means may be incorporated into the design of the device so as to lock or adhere the two sides of the seam. Preferably, the locking or adherence means are reversible so as to allow removal or manipulation of the device after initial loading and use.

The seam is preferably characterised in that a smooth surface is formed in the plane of the seam.

To prevent the device from opening, the device preferably comprises overlapping or intersecting parts, such as lips or dovetails as is known by the person skilled in the art of mechanics or moulding. The two sides of the seam may be adjoined by means of an interlocking device such as a protrusion-hole device on sides of the seam. Alternatively, to prevent slippage in perpendicular to the plane of the seam, each side of the seam may be such that each side of the seam comprises an alternating sequence of angled grooves and corresponding extrusions. Moreover, the top and bottom portion of each side of the seam may comprise alternating teeth and sockets to prevent slippage. To prevent gaping such overlapping parts and their mating surfaces of the sides of the seam may have an interlocking surface structure. The pattern of such a structure may include depressions on the mating surface of one part and corresponding elevations on the other mating part of the device.

Accordingly, in one embodiment, the overlapping parts are such that the interlocking surface structures constitute grooves. These grooves may extend radially, primarily resulting in a decreased tendency of the device to "open up" at the area corresponding to the slit or the gap. The grooves may also be orientated in a circulatory structure preventing the mating surfaces from gliding or sliding apart from each other. Additionally, the structure may comprise a combination of both elements reducing undesired movement in both of the two directions, when the device is deformed during loading of the joint.

The terms "radially" and "circular" should be understood as relative to the centre of the device or relative to the part of the device where the ligament extends through the device. "Radially" meaning e.g. grooves being located along radii from the centre, and the term "circular" meaning that e.g. the grooves are located along the periphery of a circle around the centre.

In another embodiment, the pattern includes other prominences or knobs, including pointed elevations. Thus, any structure comprising an elevation on one mating surface and a corresponding depression on the other mating surface may result in a decreased movement between the mating surfaces. Accordingly, any structure of the mating surfaces which thereby functions as an interlocking "hook" is within the scope of the invention. The mating surfaces of the curls may have an interacting profile in the form of a shape or pattern such as grooved surfaces which prevent the surfaces from sliding apart by reducing sliding movements between the mating surfaces upon loading of the device.

Another preferred embodiment of the invention relating to the seam created by the slit in the body of the device, accounts for preventing of slippage or gaping of the seam by means of a chemically treated surface of the sides of the slit. One embodiment of this aspect of the invention anticipates adherence of the two sides of the seam by means of photolytically or thermally activating a reaction between the chemically treated surfaces of the sides of the seam once the device has been loaded into the joint. Preferably, this adherence is reversible.

In another embodiment, the device may also comprise two or more separate rings each having a slit which are arranged so that the slits are orientated in such a way that no direct opening exists in the loading direction, accordingly, the slits are displaced in the direction parallel with the axis of the device. Mating surfaces of such rings may also have an interlocking structure as explained above.

In a still further embodiment, the device is in the form of a curl, wherein the ring-shaped elements together have the overall shape of a cup. Also in this embodiment, the mating surfaces may comprise grooves preventing sliding movements of the mating surfaces upon loading.

In a still further embodiment, the device may comprise minor vertical slits on the outer periphery of the device, these minor slits, e.g., having a depth of 1-5 mm may "absorb" the increasing diameter of the device upon loading. Preferably, the part of the device comprising the slits (the outer periphery) is not subject to heavy loading which could result in particulation of the edges of the device corresponding to the slits. These minor vertical slits on the outer periphery of the device may alternatively serve so as to not interfere with movable or immobile components of the joint within the cavity.

The device according to the invention may e.g. be processed by moulding of the material including extrusion and injection moulding. However, any other means for preparing the device of the desired shape could be utilised.

In addition, the device may comprise a dye or other material enabling visualisation of the device such as by X-ray.

Material Features

The material features of the device related to features conferred by the chemical composition of the device.

It is well known in the orthopaedic field to use different types of materials for prostheses that are suitable for implantation in the body. The device may be produced from any material or combination of materials suited for implants. However, it is preferable that the body of the device does not comprise of any substantial extent of metallic materials.

The combination of materials can be varied according to the properties preferred for each device. However, the body of the device, is substantially constituted of polymeric material or materials.

Preferably, the material of which the device is made is biocompatible, e.g. hemocompatible, thromboresistant, non-toxic, and/or non-carcinogenic. In addition, the material should be resistant to particulation, and the solid surface of the material should be so that the surface tension is suitable for the interaction between the material and the biological surfaces.

Biocompatibility may be assayed through in vitro tests as well as animal tests. Enzymatic biodegradation may be used as indicative of biocompatibility. Furthermore, chondrocytes and fibreblasts may be grown on the material to evaluate the compatibility.

Finally, biocompatibility may be evaluated by implanting devices of the material in animals and examining the animal and/or device after a period of time.

The device is to be substantially composed of polymeric material, particularly solid or semi-solid polymers. Polymers are the family of synthetic or natural macromolecules consisting of inorganic, organic polymers and combinations thereof. Organic polymers may be natural, synthetic, copolymers, or semisynthetic polymers. Natural polymers comprise of the class of compounds known as polysaccharides, polypeptides, and hydrocarbons such as rubber and polyisoprene. Synthetic polymers comprise elastomers such as nylon, polyvinyl resin, polyvinyl chloride, polyvinyl dichloride, polyvinylpyrrolidone, polyethylene, polystyrene, polypropylene, polyurethane, fluorocarbon resins, acrylate resins, polyacrylates, polymethylmethacrylate, linear and cross-linked polyethylene, phenolics, polyesters, polyethers, polypyrolidone, polysulfone, polyterpene resin, polytetrafluoroethylene, polythiadiazole, polyvinylalcohol, polyvinylacetal, polyvinyl oxides, and alkyds. Semisynthetic polymers may be selected from cellulosics such as rayon, methylcellulose, cellulose acetate and modified starches. Polymers may be atactic, stereospecific, stereoregular or stereoblock, linear, cross-linked, block, graft, ladder, high, and/or syndiotactic. The term graft polymer is intended to mean copolymer molecules comprising a main backbone to which side chains are attached. The main chain may be a homopolymer or copolymer and the side chains may contain different inorganic or organic constituents.

The device may comprise of cross-linked polymers elastomers such as high consistency elastomers, rubber, elastin and collagen. The material may be selected from polyurethane, elastin, collagen and combination products thereof. Alternative embodiments of materials suitable for the surface of a device according to the invention include, in addition to the materials mentioned supra and infra include hyaluronic acids and derivatives thereof.

Preferred polymeric materials are however presently believed to be those selected from the group comprising polyolefins, such as polyethylene, polypropylene, polybutene, polyisoprene, and polyvinylpyrrolidone, combinations thereof, their copolymers, and grafted polymers thereof, particularly polyethylene and polypropylene, most particularly polypropylene.

Polymers and copolymers of polypropylene or polyethylene, as well as grafted forms of each of these are particularly interesting. Moreover, surface treated forms of these polymers, copolymers or grafted polymers are of notable interest.

The structure of the material of the device or of a part of the device may be in the form of fibres and filaments which can be incorporated into the matrix in a braided, woven, spongy or spiral pattern, the fibres and filaments having reinforcing properties. The fibres may be inorganic fibres such as carbide, nitride, boride, carbon and oxide fibres, or the reinforcement may be of organic origin such as Dacron™. In a preferred embodiment the fibres are selected from polyethylene fibres, polypropylene fibres or a combination thereof. The fibres may be surface treated before incorporated into the matrix to obtain a better adhesion of fibres to matrix.

The present invention in particular relates to a device composed of material formulations intended to meet the specifications of durability, biocompatibility, etc. These properties are obtainable by treating polymer materials, such as polyethylene, polypropylene or polyvinylpyrrolidone or combinations and co-polymers thereof as well as precursor materials for polymerisation, with high-energy electrons, gamma rays, photons, microwaves, ion implantation, plasma treatment, annealing, thermal radiation or another radiation to obtain ideal durability and biocompatibility of the new, modified material. Treatment of the above-mentioned materials with radiation leads to cross-linking of polymers and thereby generating new, modified materials. Preferably, the polymer material is a cross-linked polypropylene material. In another embodiment the polymer material is a cross-linked polyethylene material.

A device according to the invention preferably comprises at least a first polymeric component and a second polymeric component, wherein the chain length of the first polymeric component is longer than the chain length of the second polymeric component. The first polymeric component is providing the physical properties, such as strength of the device as discussed below. Due to the longer chain length the strength, in particular the tensile strength, of the device is increased. The chain length of the first polymeric component is preferably above 100 monomer units, such as above 120 monomer units, preferably above 150 monomer units. The chain length of the second polymer is preferably at most 99% of the chain length of the first polymer, such as at most 95%, such as at most 90%, such as at most 80%, such as at most 70%, such as at most 60%, such as at most 50%.

In one embodiment the device comprises a body constituted by the first and the second polymeric components. The body may optionally be treated in order to optimise the properties such as surface properties, biocompatibility and/or low friction. By the term "body of the device" is meant the part of the device providing the strength properties as well as the resiliency properties.

In another embodiment the device comprises a body constituted by the first polymeric component, whereas the second polymeric component provides optimised surface properties.

In a preferred embodiment the first polymeric component is selected from polymers having a carbon-backbone.

The first polymeric component may be selected from polyacrylates, polystyrene, polyethers, polytetrafluorethylene, polyvinylalcohol, polyethylene, and polypropylene.

When the body is constituted by two components, the second polymeric component may be selected from polyacrylates, polystyrene, polyethers, polytetrafluorethylene, polyvinylalcohol, polyethylene, and polypropylene. Preferred combinations for the first and the second polymeric component are polyethylene and polypropylene, polyethylene and polyethylene, or polypropylene and polypropylene, in the latter two cases, the first and the second polymeric components is comprised of identical monomers, whereas the polymers thereof are of different chain length. When the monomers of the two polymeric components are identical the prosthetic device is preferably compounded to form a bidispergent system.

The second polymeric may in a preferred embodiment be a cross-linked polymer. The combination of a polymer having a high chain length and a polymer having a shorter chain length, but being cross-linked provides a strong device yet having the resilient properties necessary for the device.

Furthermore, radiation also allows grafting of polymers onto existing polymer surfaces, resulting in new mechanical properties as well as new surface properties. In this manner, the resulting modified polymer device can be processed to meet the necessary requirements of durability and biocompatibility.

Polymers may be prepared by methods known to the person skilled in the art. Chemical catalysis, thermal induction or photo induction are anecdotal non-limiting examples of methods of preparing the polymers. The cross-linking of the polymers or grafting may be done by radiation or other methods known to the person skilled in the art.

The properties of the materials to be obtained by these cross-linking and grafting processes are preferably i) resistance to tear and wear; ii) good compressibility; iii) flexibility and surface properties which will allow wetting with biological fluids, and/or eventually allow growth of chondritic cells onto the prosthetic device.

Typically, the device is prepared by a process comprising of the following steps:

The prosthetic devise is formed by casting the pure polymer or a blend of polymers in a mould of specified dimensions. The polymer is chosen from the above mentioned polymers.

After hardening the cast material as formed, or after swelling in a suitable solvent, the device is subjected to high-energy electrons, gamma rays or another radiation in order to create cross-linking which will modify the mechanical properties of the cast material to meet the preferred specifications.

Finally, eventually after removal of the swelling solvent, the surface of the cast material is treated to achieve good surface properties as described above.

The surface of the device can subsequently be treated to modify surface properties such as wetting ability and/or biocompatibility. This surface treatment can be performed by plasma treatment, chemical grafting or by a combination of plasma treatment and chemical grafting. The surface of the device contacting with the articulating surfaces of the joint may be of such a material which forms a uniform contact surface reducing the overall contact stress per unit area, and thereby avoiding corrosion of the articulating surfaces of the joint. Accordingly, the material contacting with the biological surfaces may be smooth, biocompatible, preferably self-lubricating, and it should be wear-resistant so that powder generated due to wear is avoided in that this could otherwise result in foreign matter reactions and cause further trouble to the function of the joint.

Furthermore, the surface material should preferably be a material or a combination of materials having self-repairing properties so that fissures, cracks or other ruptures on the surface do not exceed uncontrollable levels. However, the surface material is preferably continuous with the material of the rest of the device, e.g. the material may gradually merge into the material of the inner core or matrix of the device.

The surface of the material may be chemically treated so as to soften, rigidify or lubricate the surface of the device or parts thereof. The surface of the material may be coated so that the coating confers these properties, or may be treated so as to chemically alter the surface of the device so as to confer any of these properties. Alternatively, certain polymer surfaces may be modified by means of thermal or photolytic energy.

Also the surface treatment may be provided by incorporating surface treatment polymer, such as polyvinyl pyrrolidone, into the matrix to maintain the good surface properties.

Independent of whether the body of the device comprises one or two components, it is preferred that the body of the device is provided with a treatment resulting in a functional surface of the device being wettable by the joint fluid normally present in the joint cavity, in oder to decrease any friction between the device and joint parts, such as bone, cartilage, ligaments and mucosa.

Without being bound by theory it is also believed that a wetted surface reduces the risk of having the immune system recognising the device when implanted, which would otherwise lead to adverse effects of the device.

By the term "functional surface" is meant the external surface of the device, ie. the surface contacting joint cavity parts. Since the body of the device is often produced as one, two or even three dimensional networks, internal surface may be present in the body, said internal surfaces often corresponding with the external surfaces.

Thus, the prosthetic device preferably comprises a third polymeric component, said third polymeric component being different from the first and/or the second polymeric component. The third component will preferably be grafted to the body of the device and result in the improved surface properties. The third polymeric component is preferably selected from polyethylene oxides, and polyvinylpyrrolidon, most preferably from polyvinylpyrrolidon.

When the body is comprised of one component, such as wherein the first polymeric component comprises a copolymer of polyethylene and polypropylene or wherein the first polymeric component is a cross-linked polymer, the second polymer may be grafted to the first polymer and act as the third polymeric component as described above.

Preferred devices are composed of:
A body of polyethylene having polyvinylpyrrolidone grafted thereto
A body of two polyethylene polymers of different chain lengths having polyvinylpyrrolidone grafted thereto
A body of polypropylene having polyvinylpyrrolidone grafted thereto
A body of two polypropylene polymers of different chain lengths having polyvinylpyrrolidone grafted thereto
A body of a copolymer of polyethylene and propylene having polyvinylpyrrolidone grafted thereto
A body of a polyethylene and a copolymer of polyethylene and polypropylene having polyvinylpyrrolidone grafted thereto
A body of polypropylene and a copolymer of polypropylene and polyethylene having polyvinylpyrrolidone grafted thereto
A body of polyethylene having 2-vinylpyrrolidone grafted thereto
A body of two polyethylene polymers of different chain lengths having 2-vinylpyrrolidone grafted thereto
A body of polypropylene having 2-vinylpyrrolidone grafted thereto
A body of two polypropylene polymers of different chain lengths having 2-vinylpyrrolidone grafted thereto
A body of a copolymer of polyethylene and propylene having 2-vinylpyrrolidone grafted thereto
A body of a polyethylene and a copolymer of polyethylene and polypropylene having 2-vinylpyrrolidone grafted thereto
A body of polypropylene and a copolymer of polypropylene and polyethylene having 2-vinylpyrrolidone grafted thereto Mechanical Features The mechanical features of the device relate to properties conferred by the structural and/or material features of the device.

The present invention provides new material formulations intended to meet the specifications of a durable, biocompatible device. The present device may be produced from materials hitherto unknown for implants as long as the following material features and requirements are met and that the materials have optimised properties relating to:
Mechanical, chemical and physical stability and optimised tribological properties.
Good biocompatibility.
Resistance to elevated temperature (sterilisation).
Affinity to the surrounding biological components.
Dynamic characteristics suitable for stress distribution.

Furthermore, as stated supra, radiation allows grafting of polymers onto existing polymer surfaces, resulting in new mechanical properties as well as new surface properties. In this manner, the resulting modified polymer device can be processed to meet the necessary requirements of durability and biocompatibility.

The surface of the device can subsequently be treated to modify surface properties such as wetting ability and/or biocompatibility. This surface treatment can be performed by plasma treatment, chemical grafting or by a combination of plasma treatment and chemical grafting.

The properties of the new materials to be obtained by these cross-linking and grafting processes are: resistance to tear and wear, good compressibility and flexibility and surface properties which will allow wetting with biological fluids, and/or eventually allow growth of chondritic cells onto the prosthetic device.

It is believed that the surfaces of the device in contact with biological surfaces within the joint will be subject to interactions resulting from frictional resistance, since only part of the sliding/rotating movement of the joint will take place by internal movement of the device.

The surface material should also be elastic in order to allow deformation of the shape without damage to the continuity of the surface but should on the other hand also secure stability of the overall shape of the device.

The inner matrix of the device should be suitable for stress distribution such as materials being pressure absorbent, having elongation properties and rigidity. Preferably, the device is composed of a single homogenous material or a combination of materials having the surface properties mentioned above as well as the relevant dynamic characteristics suitable for stress distribution. Preferably, the device comprises exclusively of solid or semi-solid non-metallic material.

Mechanical properties for certain relevant polymers are described by Szycher (Szycher, M. (editor), sponsored by SPE, Society of Plastics Engineers, Inc. Biocompatible Polymers, Metals, and Composites, pp. 725-727, 757-61).

Mechanical properties of polymers are controlled by the elastic parameters, the three moduli: elastic, shear, and compressive moduli. These parameters are theoretically interrelated. A modulus is the ratio between the applied stress and the corresponding deformation. The reciprocals of the moduli are called compliancies. The three elastic moduli have the dimension: force per unit area, (N/m² or Pa). Polymers are not normally ideal elastic bodies, but under load they show (time dependant) viscoelastic properties. By taking the load into consideration, the properties should be viewed according to this dilemma. Also, ideal elastic properties and ultimate properties, are influenced by the viscoelastic properties.

Ultimate tensile strength is a measure of the stress required to cause the material to rupture in tension. Ultimate elongation is the percent stretch of the material before it ruptures in tension. Elongation (%) is measured as $$\text{Elongation (percent)} = \frac{S_B - S_o}{S_o} \times 100$$

where $S_B$=observed distance between bench marks of the stretched specimen at rupture, and $S_o$=the original distance between bench marks.

TABLE 1

Elastic parameters and their definitions

| Elementary mode of deformation | Elastic parameter | Symbol |
|---|---|---|
| Isotropic (hydrostatic) compression | Bulk modulus bulk compliance or compressibility | K κ (κ = 1/K) |

TABLE 1-continued

Elastic parameters and their definitions

| | | |
|---|---|---|
| Simple shear | Shear modulus or rigidity | G |
| | Shear compliance | J (J = 1/G) |
| Uniaxial extension | Tensile modulus or Young's modulus | E |
| | Tensile compliance | S (S = 1/E) |
| Any | Poisson ratio | ν |

| Symbol | Definition |
|---|---|
| K | $\dfrac{\text{Hydrostatic Pressure}}{\text{Volume change per unit volume}} = \dfrac{p}{\Delta V/V_0} = \dfrac{pV_0}{\Delta V}$ |
| κ (κ = 1/K) | reciprocal of foregoing |
| G | $\dfrac{\text{Shear force per unit area}}{\text{Shear per unit distance between shearing surfaces}} = \dfrac{F/A}{\tan\gamma} = \dfrac{\tau}{\tan\gamma} \approx \dfrac{\tau}{\gamma}$ |
| J (J = 1/G) | reciprocal of foregoing |
| E | $\dfrac{\text{Force per unit cross-sectional area}}{\text{Strain per length}} = \dfrac{F/A}{\ln(L/L_0)} = \dfrac{\sigma}{\varepsilon} = \dfrac{F/A}{\Delta L/L_0}$ |
| S (S = 1/E) | reciprocal of foregoing (strain/stress) |
| ν | $\dfrac{\text{Change in width per unit width}}{\text{Change in length per unit length}} = \dfrac{\text{lateral contraction}}{\text{axis strain}}$ |

Examples of ranges of the mechanical properties of the device are mentioned below. However, it should be contemplated that not all of the following characteristics may be fulfilled by the material of the prosthetic device since, as explained above, the numerous properties of the material are theoretically interrelated. Accordingly, conflict in fulfilling all parameters within the stated ranges may occur.

In one embodiment, the prosthetic device according to the invention is a device wherein the material of the device or at least the part of the device which exerts the pressure distribution and/or the part which exerts the sliding/rotating movement in the joint when the joint is loaded has/have one or more of the following properties (under biological conditions (37° C., physiological salinity)): A compressive modulus (K) of at least 2000 MPa, a shear modulus (G) of at least 1 MPa and an elastic module (E) of at least 10 MPa.

Furthermore, certain requirements to the material under stress with forces that ultimately leads to disintegration can be expressed. Based on the elasticity parameters for the material, the properties of the material with respect to pressure, elongation, torsion and displacement in the range where the material responds elastic can be estimated. The ultimate limits should preferably be within ±20% of the range of elastic response. As a consequence thereof, the limits for the ultimate properties (ultimate compression strength, tensile strength, torsional strength, shearing strength) can be derived.

Furthermore, the material should have an "ultimate percentage elongation" of at least 20%.

The materials according to the invention may be a "quasi elastic" material. Y. Shikinami and H. Kawarada, Biomaterials 19, 1998, pp. 617-635, discuss that many materials of biological origin, has a J-form in a stress vs strain curve, whereas may synthetic materials has an S-form.

Preferably, the critical surface tension ($\gamma_c$) values should be within the "zone of biocompatibility" corresponding to the range of about 20-30 dynes/cm (as defined by Lelah M. D., Cooper, S. L., Polyurethanes in Medicine- CRC Press, Inc. Boca Raton, Fla., pp. 59-62 and 92-93).

In one embodiment of combined features, the diameter of the device is about 35 mm and the thickness is about 5 mm and the material of at least a part of the device has an ultimate percentage elongation of at least 20% corresponding to an ultimate angle of twist of about 90°.

In another such embodiment, the diameter of the device is about 35 mm and the thickness is about 10 mm and the material of at least a part of the device has an ultimate percentage elongation of at least 20% corresponding to an ultimate angle of twist of about 90°.

In a further embodiment, the diameter of the device is about 35 mm and the thickness is about 10 mm and the material of at least part of the device has an ultimate percentage elongation of at least 20% corresponding to an ultimate angle of twist of about 180°.

Insertion

It is also an object of the present invention to provide a method for introducing a device according to the present invention into a joint. The method comprises:
a) locking the device to an intra-articular component and thereby fixing or retaining the device in the joint cavity in a manner which is substantially non-invasive with respect to cartilage and bone natively present in the joint cavity.

The method may further comprise any of the following steps before locking the device to the intra-articular component in the joint:
i) exposing the joint capsule by conventional surgery procedures,
ii) penetrating the joint capsule into the joint space leaving a passage for
iii) introducing the prosthesis into the joint capsule via the passage, the prosthesis having a shape suitable for being introduced through this passage.

Locking the device to the intra-articular component and thereby fixing or retaining the device in the joint cavity in a manner which is substantially non-invasive with respect to cartilage and bone natively present in the joint cavity may include encircling a ligament present in the joint with a ring-shaped element of the device such as a ring-shaped device having a slit extending from the periphery of the device to the central opening of the "ring".

The method may further comprise the steps of deforming the prosthetic device into a reduced volume or a slender shape before locking the device to the intra-articular component.

In the case of insertion into a hip joint, the insertion of the device is preferably performed after penetration through the head of the rectus femoris muscle leaving a passage having a substantial width for introducing means into the joint capsule without alteration of the function of the capsule after the surgery.

Means or instruments for inserting the device into the joint space can be in the form of forceps comprising means for deforming the device into a minor volume or a more slender shape and may comprise means for grasping around the intra-articular component to which the device is capable of interlocking.

The forceps may further comprise means for locking the device around or substantially around the intra-articular component and optionally means enabling the forceps to be withdrawn without withdrawing the device.

Thus, a further object of the invention relates to a kit comprising:

a) an intra-articular prosthetic device for a joint having
   a.1) a spacer function and/or capability to exert pressure distribution and/or sliding/rotating movement of the joint by an internal movement of the device by means of a resilient member, and
   a.2) a locking mechanism adapted to fix the device to an intra-articular component by means of an element of the device surrounding the component in such a manner that displacement of the device is limited by inter-locking with the component; and
b) an instrument for inserting the prosthetic device into a joint cavity Preferably, the elements of the kit should be sterile.

The instrument b) may further comprise one or more of the following means b.1 to b.4:

b.1) means for deforming the prosthetic device into a reduced volume or to a slender shape and keeping this volume or shape upon introduction of the device to the joint;
b.2.) means for grasping or encircling the intra-articular component to which the element of the prosthetic device is capable of inter-locking;
b.3.) means for leaving the prosthetic device in the joint with the element of the prosthetic device surrounding an intra-articular component; and
b.4.) means for retracting the instrument from the joint.

It is contemplated that each of the means of b.1.), b.2.), b.3.) and b.4.) may be connected to or form part of a handle. Moreover, the resilient member of a.1) and the element surrounding the intra-articular component of a.2) may constitute the prosthetic device.

The means of b.2.) for grasping or encircling the intra-articular component may comprise an incision of the instrument which, in situ, is able to substantially retain the element within the "legs" of the incision.

Biological Activity of the Device

When inserted in the joint cavity the device is capable of alleviating the pain and other symptoms related to damaged cartilage, such as improving movements. Furthermore, the device may be capable of healing the sick bone's structure and/or cartilage structure- in hole of partly.

For example the device may facilitate creation of new cartilage and/or minimise destruction, such as fibrillation and/or fragmentation, of cartilage by relieving the pressure on the residual cartilage/bone in the joint Furthermore, the device may comprise biological active additives. Medication or biological active substances can be used as additive to the device to facilitate healing, minimise destruction or with other therapeutic goals, such as pain relieve, anti-inflammation, oncology treatments, stimulation of bone growth, and/or anti-infectious agents. Also, biological osteogenic or chondrogenic, chondral inductive, and/or chondral conductive materials may be added to the device. In particular patients suffering from osteoporosis or other bone degenerating conditions may benefit from having devices comprising osteogenic inductive materials implanted.

The medication or biological active substances can be used as additive to the device to facilitate cell growth, such as osteocytes, osteoblasts, chondrocytes, chondroblasts, mesenchymal cells. Cartilage inducing factor may for example be the factors described in U.S. Pat. No. 4,774,322 and U.S. Pat. No. 4,843,063

The device itself can be used as a growth medium and/or network for the natural or artificial cells, such as chondrocytes.

The device is capable of being formed to suit any joint cavity of animals or human beings, therefore the device may for example be formed to fit into any one of the following joints:

Hip joint, knee joint, ankle joints, shoulder joint, elbow joints, wrist, fingers, spinal column joints, such as for substituting intervertebral discs, and the jaw joint.

EXAMPLES

Figure 1:
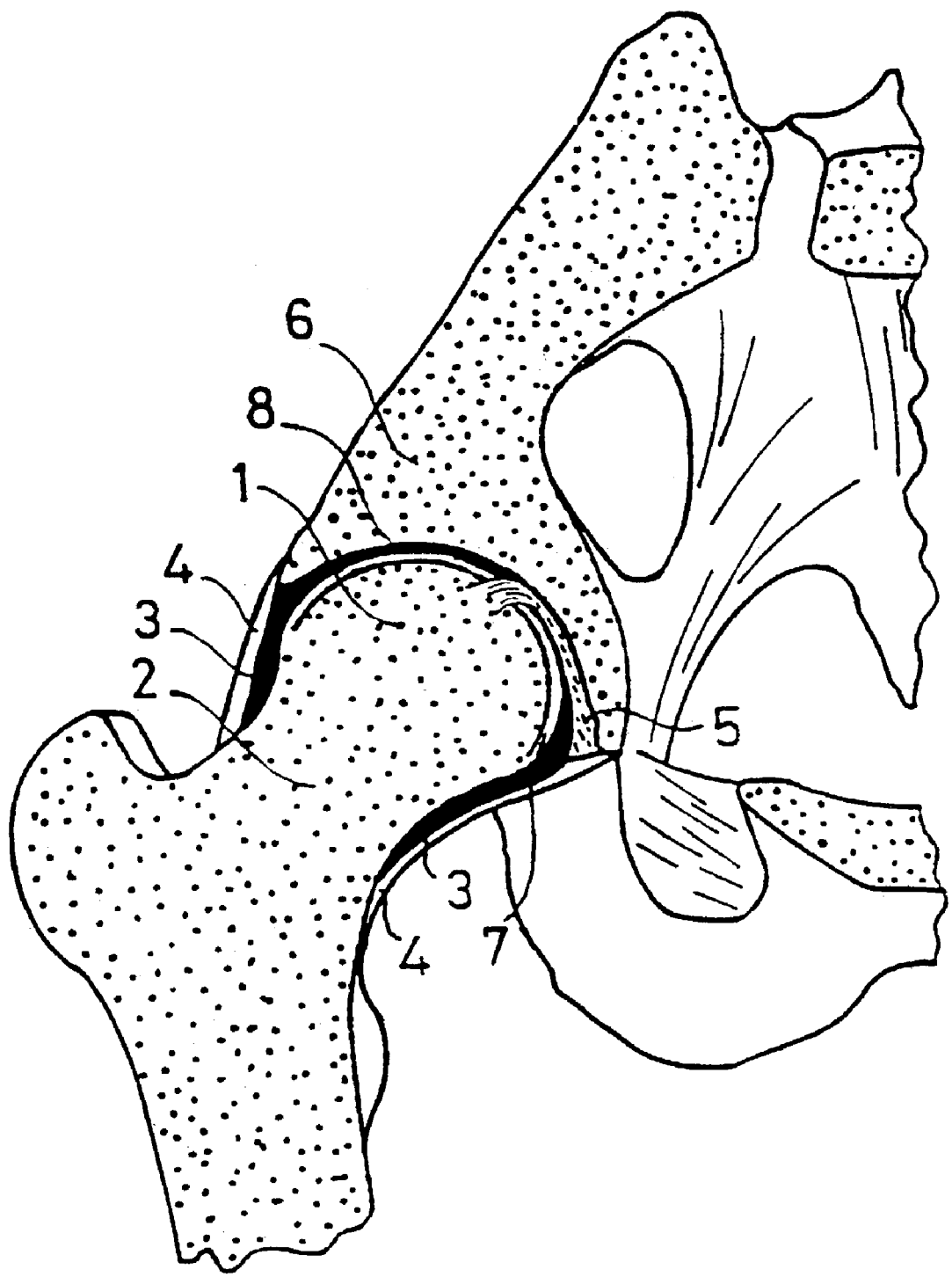
FIG. 1 shows a cross sectional perspective view of a human hip joint.

A Procedure for Producing a Device According to the Invention

Example 1

The device is produced using compression molding. A preformed fibre network consisting of polyethylene fibres (Dyneema®, DSM Holland) wetted with a plastomer of the polyethylene type (Hostalen®, DSM Holland) is heated and compressed into the shape of the finished device in an appropriate mold. The heating procedure ensures that the plastomer flows together. The heating temperature is selected below the melting temperature of the fibre crystallites in order not to loose the crystallinity of the polyethylene fibres, ie. below 140° C., and above the melting temperature of the polyethylene plastomer, ie. in the range between 100-140° C. Subsequent cross-linking of both fibres and plastomer is obtained using treatment with accelerated electrons followed by annealing. As the cross-linking process takes place in the amorphous polyethylene regions, the optimal dose will depend on the fraction of amorphous polyethylene in the final device. The optimal radiation dose is close to the gelation dose of polyethylene and thus lie between 30 and 300 kGy (3-30 Mrad). The purpose of annealing is to eliminate long living free radicals by a heat treatment of 80° C. for about 12 hours in vacuum. Subsequent surface grafting with polyvinylpyrrolidone is obtained by irradiating the device surrounded by a solution of polyvinylpyrrolidone, wherein the irradiation dose is in the range between 10 and 100 kGy. After the grafting procedure the device is washed with water to remove ungrafted polyvinylpyrrolidone.

Example 2

The device is produced as described in Example 1, except that polyvinylpyrrolidone is substituted with a solution of 2-vinylpyrrolidone.

Example 3

The device is produced as described in Example 1, except that polyvinylpyrrolidone is substituted with a solution of a combination of polyvinylpyrrolidone and 2-vinylpyrrolidone.

A Surgical Procedure for Insertion of a Prosthetic Device According to the Invention into the Hip Joint Antero-lateral exposure of hip. Modified Smith-Petersen approach (Smith-Petersen M. N.; Approach to and exposure of the hip joint for mold arthroplasty. *J. Bone Joint Surgery* 1949; 31 A: 40)

Technique: Position of patient: The patient may lie supine on the operation table. Traction may be applied by use of bone traction in the femoral condyles, or by soft tissue traction in a boot as used when osteosynthezising a proximal femoral hip fracture. A counter extension may be applied by an external pin placed on the symphysis. A small sandbag may be placed under the buttock of the affected side to rotate the trochanter slightly forwards. Some may prefer the postero-lateral approach with the patient in the lateral position, but the approach may be more difficult with respect to reaching the teres ligament in the hip joint.

Incision: The incision forms an angle open anteriorly. Its upper limb begins 4 cm behind the anterior superior spine of the ileum and extends obliquely backwards to the tip of the greater trochanter. The lower limb of the incision extends vertically downwards from the greater trochanter for 5 cm. The skin flaps are mobilised from the underlying deep fascia, which is cleared of adherent adipose tissue.

The deep exposure: When the deep fascia has been incised, the interval between the tensor fascia latae muscle anteriorly and the gluteus medius posteriorly is identified immediately proximal to the antero-superior corner of the greater trochanter. This interval is widened by separating the fibres with dissecting scissors and is continued proximally. Towards the crest of the ileum, the two muscles are blended more closely and have to be separated by sharp dissection with scissors. The space between the muscles is opened up by stripping part of the muscle origins from the outer aspect of the wing of ileum. Closer to the trochanter, the gluteus minimus may also be partly raised from the bone and retracted posteriorly. In the lower half of the wound, the capsule of the hip joint now comes into view with, immediately above it, the reflected head of the rectus femoris muscle. The reflected head and the anterior part of the capsule is to be preserved and is opened by an H-shaped incision and flaps turned proximally and distally.

The maximal traction is now performed. A space in the joint of 1.5 cm is needed. Relevant elongation of muscles and tendons may be performed. Adduction tenotomy may be performed by a small stab wound incision, whereas the rectus can be reached by the antero-lateral approach.

The grab-forceps with the hip joint device is now inserted, and the retractor may help to catch the teres ligament of the head of femur.

The hip joint must be tested to verify the stability of the hip joint device. The hip ring is allowed to space the relaxed joint by 0.8-1.5 cm.

The capsule is closed with two or three Vicryl sutures, after which the separated muscles are likewise approximated with interrupted sutures. The skin is closed with deep tension sutures and skin edge sutures. A suction drainage may be used according to the circumstances.

DETAILED DESCRIPTION OF THE DRAWINGS

FIG. 1 shows a cross sectional perspective view of a human hip joint where the femoral head 1 is shown in connection with the femoral neck (collum femoris) by the joint cavity 3 (cavum articulare). The joint cavity 3 is separated from the outside by the joint capsule 4 (capsula articulare). From the femoral head 1, ligamentum femoris 5 extends through the joint cavity 3 between the acetabulum 6 and the cartilage 7 covering the femoral head 1. Ligamentum femoris 5 is anchored in the bone of the femoral head at one end and the ligament fibres are attached to the acetabulum 8 which is part of the hip bone 6 (os coxae).

Figure 2:
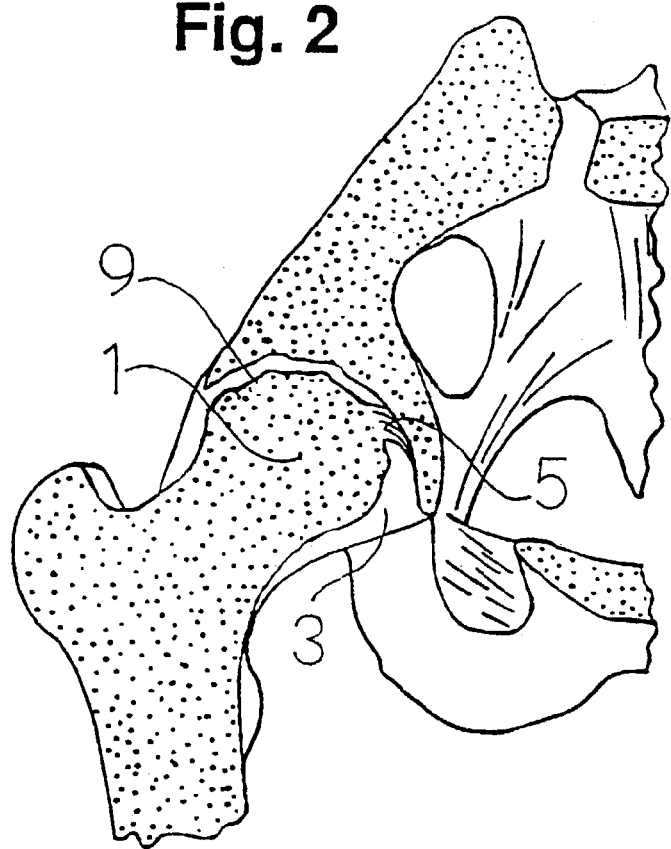
FIG. 2 shows a cross sectional perspective view of the hip bone corresponding to FIG. 1.

FIG. 2 shows a cross sectional perspective view of the hip bone corresponding to FIG. 1. However, e.g. due to damage of the femoral head, the cartilage is missing and the bone of the femoral head is in direct contact with the acetabulum. Both the surface of the acetabulum and the surface 9 of the femoral head 1 are damaged. The intact ligamentum femoris 5 extends through the joint cavity 3.

Figure 3:
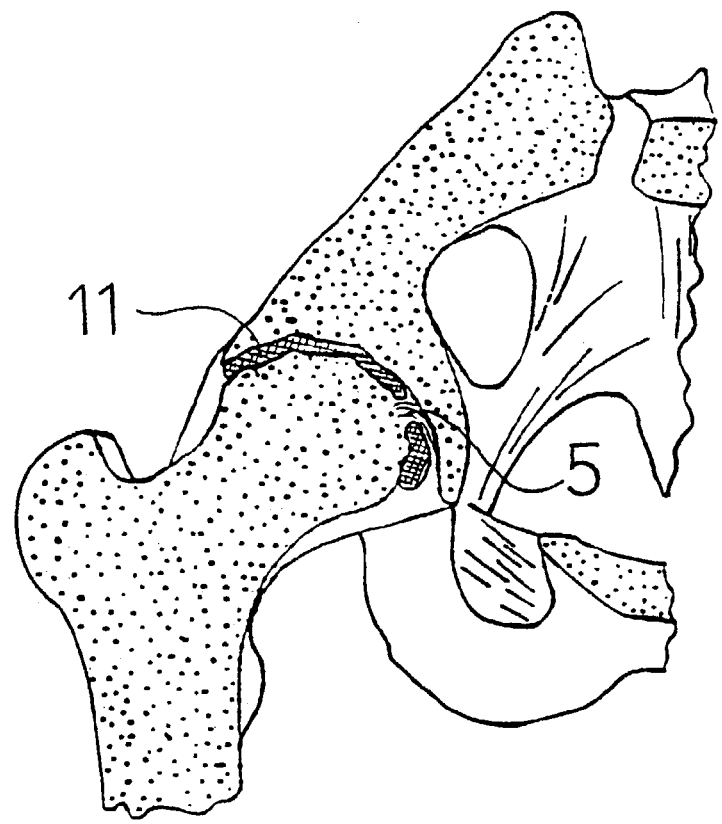
FIG. 3 shows a cross sectional perspective view of the human hip bone in which one embodiment of a device 11 according to the invention is shown in situ.

FIG. 3 shows a cross sectional perspective view of the human hip bone in which one embodiment of a device 11 according to the invention is shown in situ. Ligamentum femoris 5 extends from its attachment of the femoral head through the device and is located between the acetabulum and the upper surface of the device.

Figure 4:
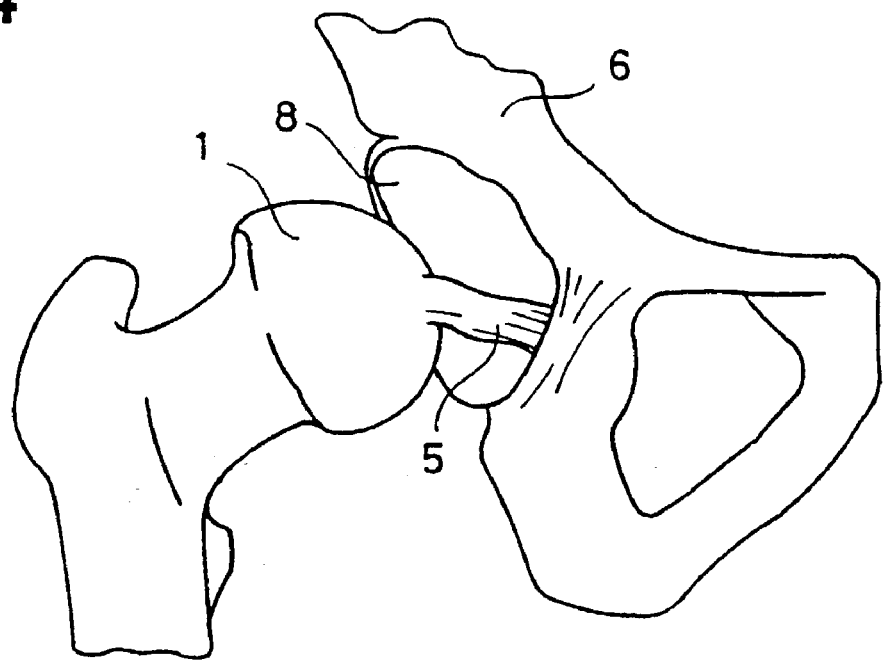
FIG. 4 shows a perspective view of the human hip joint in which the femoral head has been retracted from the acetabulum.

FIG. 4 shows a perspective view of the human hip joint in which the femoral head 1 has been retracted from the acetabulum 8. Ligamentum femoris 5 is anchored in the femoral head at one end the other end is located in the acetabulum 8 of the hip bone 6.

Figure 5:
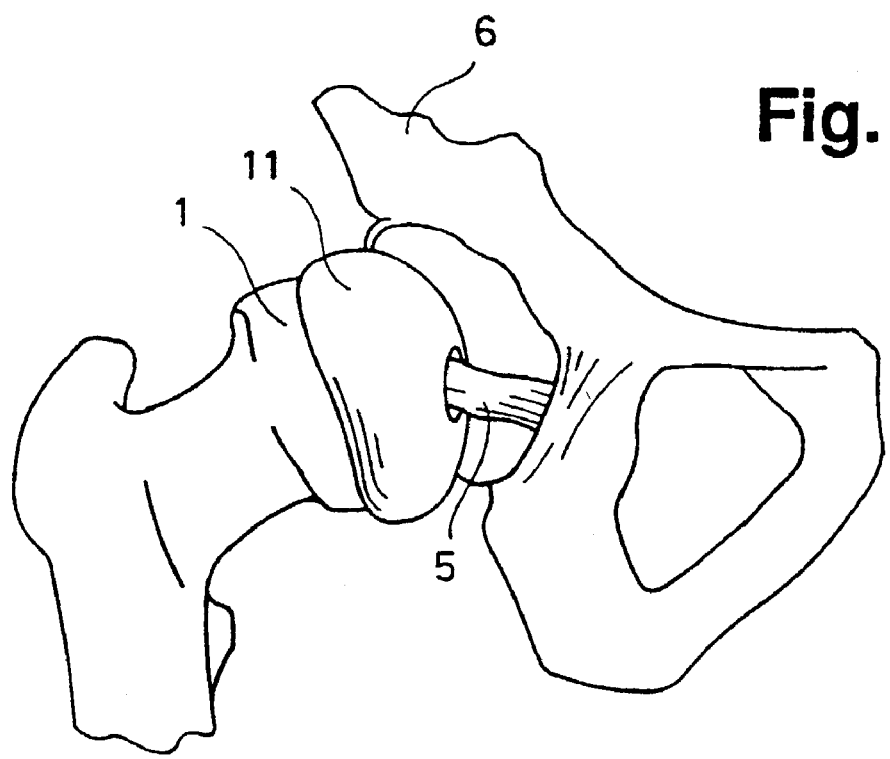
FIG. 5 shows a perspective view in which one embodiment of a device 11 according to the invention is located in situ.

FIG. 5 shows a perspective view in which one embodiment of a device 11 according to the invention is located in situ covering the femoral head and surrounding ligamentum femoris 5 which thereby extends through the device 11. When the ligament is surrounded by the device, replacement of the device is prevented. However, circular movement around the substantially central ligament is possible.

Figure 6:
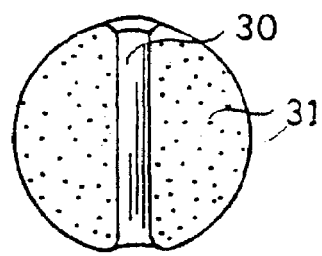
FIG. 6 shows a cross sectional perspective view of an embodiment of the device according to the invention disclosing a device having a globular shape.

FIG. 6 shows a cross sectional perspective view of an embodiment of the device according to the invention disclosing a device having a globular shape in which a tubular passage 30 extends through the device 31. The passage extends along the central axis from one pole to the opposite pole.

Figure 7:
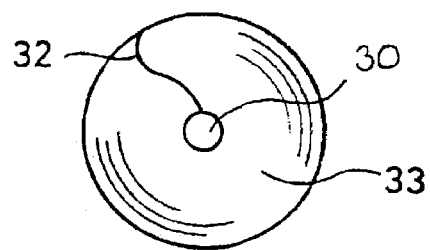
FIG. 7 shows an elevational perspective view of a spherically shaped device.

FIG. 7 shows an elevational perspective view of a spherically shaped device having a central tubular passage 30 extending through the device 33 and a slit 32 extending from the outer surface of the device and through the body of the device into the central passage 30. The slit may be curl-formed in the radial direction with the axis of the tubular passage being the center.

Figure 8:
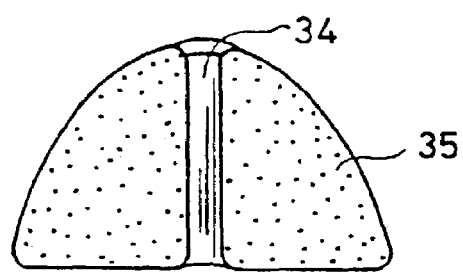
FIG. 8 shows a cross sectional perspective view of a cup-shaped device.

FIG. 8 shows a cross sectional perspective view of a cup-shaped device having a central passage 34 extending from the convex upper part to the flattened bottom of the device 35.

Figure 9:
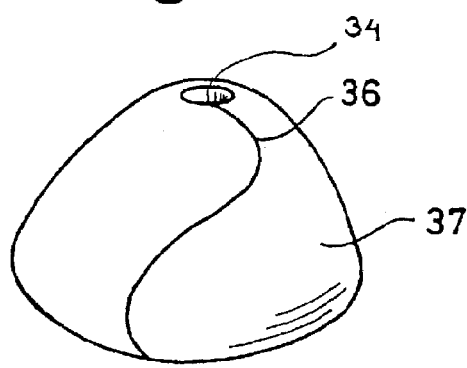
FIG. 9 shows a perspective view of a cup-shaped device according to the device shown in FIG. 8.

FIG. 9 shows a perspective view of a cup-shaped device according to the device shown in FIG. 8. The device 37 has a slit 36 extending from the surface of the device into the central passage 34 shown as a hole of the upper part of the device.

Figure 10:
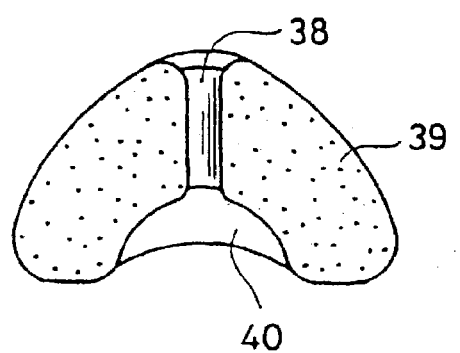
FIG. 10 shows a cross sectional perspective view of another embodiment of a cup-shaped device.

FIG. 10 shows a cross sectional perspective view of another embodiment of a cup-shaped device 39 having an upper convex surface and a lower surface 40 which is concave and forms a half spherical cavity having a passage 38 which extends to the upper convex surface of the device.

Figure 11:
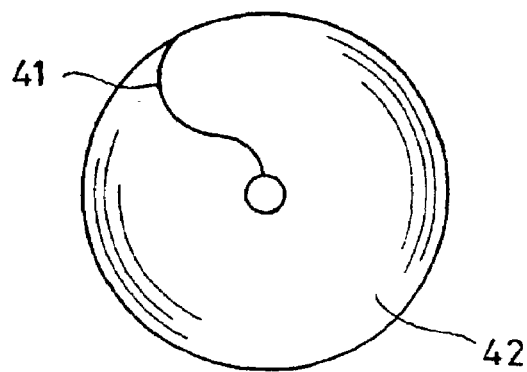
FIG. 11 shows an elevational perspective view of the embodiment of a device as shown in FIG. 10.

FIG. 11 shows an elevational perspective view of the embodiment of a device as shown in FIG. 10. The slit 41 has a substantially S-shaped course which extends through the device 42 from the centre to the periphery of the device.

Figure 12:
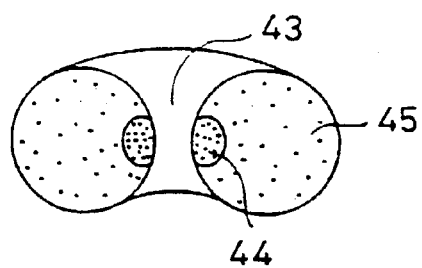
FIG. 12 shows a cross sectional perspective view of a ring-shaped device.

FIG. 12 shows a cross sectional perspective view of a ring-shaped device. The central part 44 is composed of a reinforced material compared to the rest of the device material 45. The central surface 43 represents the part of the device in contact with the ligament.

Figure 13:
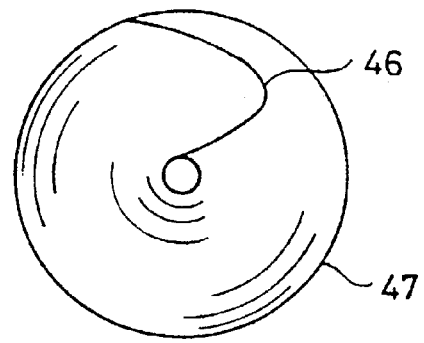
FIG. 13 shows an elevational perspective view of a ring-shaped device.

FIG. 13 shows an elevational perspective view of a ring-shaped device in which the slit 46 has a substantially tongued course. Such a tongued course of the slit may represent overlapping parts in a plane substantially perpendicular to an axis through the central passage of the device. As appears from the figure, the slit 46 extends from the central hole to the outer periphery 47 of the device.

Figure 14:
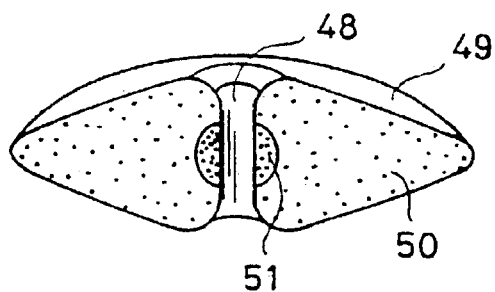
FIG. 14 shows a cross sectional perspective view of a substantially disc-shaped embodiment of the device.

FIG. 14 shows a cross sectional perspective view of a substantially disc-shaped embodiment of the device showing the central passage 48 extending from the outer surface 49 through the device. A part of the central material 51 is shown as reinforced compared to the rest of the material 50 of the device.

Figure 15:
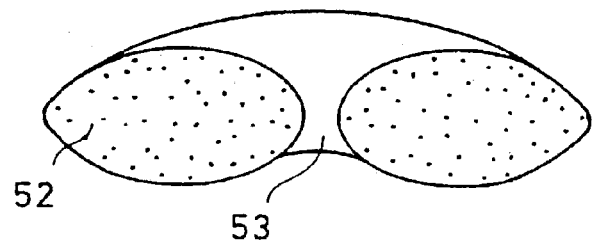
FIG. 15 shows a cross sectional perspective view of a ring-formed embodiment of the device consisting of a substantially homogeneous material.

FIG. 15 shows a cross sectional perspective view of a ring-formed embodiment of the device consisting of a substantially homogeneous material 52. As shown, the periphery of the device, where the upper and lower surface meet, is less rounded compared to the corresponding central part 53.

Figure 16:
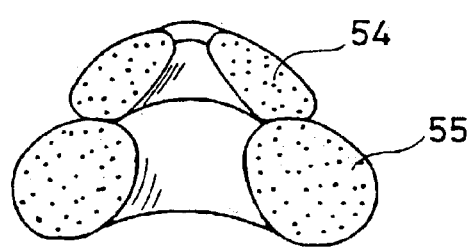
FIG. 16 shows a cross sectional perspective view of a double ring-shaped embodiment of the device.

FIG. 16 shows a cross sectional perspective view of a double ring-shaped embodiment of the device (a device consisting of two units) having the overall shape of a cup comprising a cavity corresponding to the lower surface which is in contact with the femoral head. The upper ring 54 being smaller than the lower ring 55. The device may comprise rings of different materials.

Figure 17:
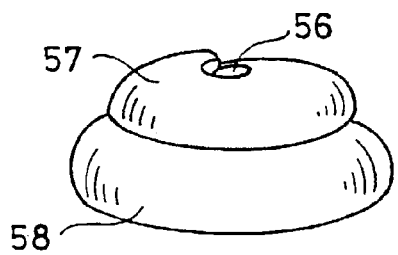
FIG. 17 shows a perspective view of an embodiment of a device comprising two ring-shaped elements.

FIG. 17 shows a perspective view of an embodiment of a device comprising two ring-shaped elements. The upper ring 57 of the device may continue in the lower ring 58 around the axis of the central hole 56. Accordingly, the device, having a slit which has the course between the surfaces of the upper and the lower rings, can be arranged around the ligament by a rotating movement until the ligament is positioned in the centre of such curly device.

Figure 18:
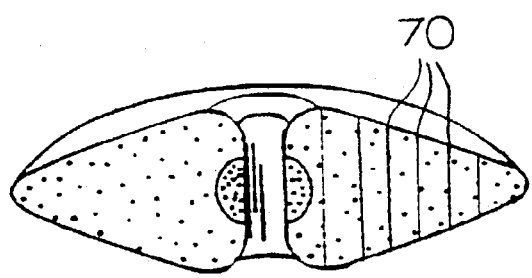
FIG. 18 shows a cross sectional perspective view of an embodiment of the device in showing vertical lines corresponding to grooves on the surfaces representing a slit.

FIG. 18 shows a cross sectional perspective view of an embodiment of the device in which the vertical lines 70 represent top and bottom, respectively, of grooves forming a zigzag-shaped slit extending in the radial direction from the central hole to the periphery as well as from the upper to the lower surface of the device.

Figure 19:
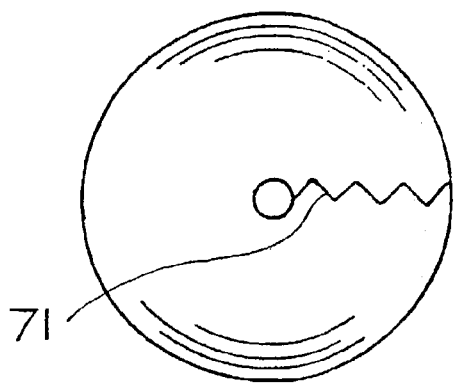
FIG. 19 shows an elevational perspective view of an embodiment of the device corresponding to the one shown in FIG. 18.

FIG. 19 shows an elevational perspective view of an embodiment of the device corresponding to the one shown in FIG. 18. The zigzag-shaped slit 71 has a substantially radial direction.

Figure 20:
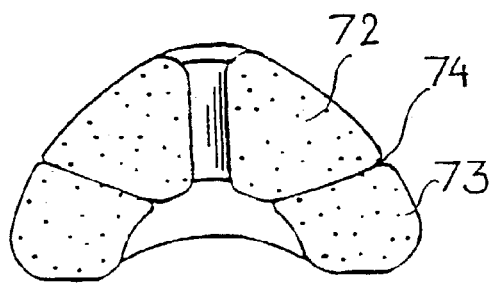
FIG. 20 shows a cross sectional perspective view of a device substantially similar to the one shown in FIG. 17.

FIG. 20 shows a cross sectional perspective view of a device substantially similar to the one shown i FIG. 17 in which the two ring-shaped elements 72 and 73 of the curl together form an upper spherical surface fitting into the acetabulum and comprising a lower cavity which is also of a spherical shape which fits on the femoral head. The upper ring-shaped element 72 comprises a central passage for the ligament which is thereby surrounded by the upper ring. The contact zone 74 constitutes part of the slit. In another embodiment each ring-shaped element comprises its own separate slit whereby the device comprises separated rings.

Figure 21:
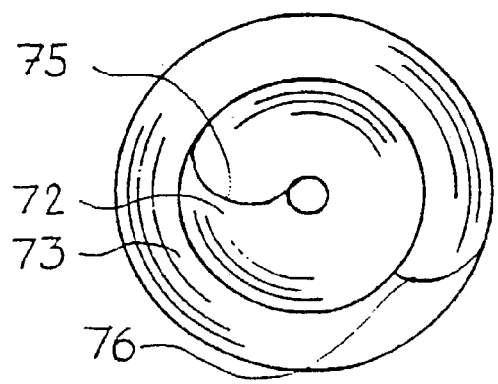
FIG. 21 shows an elevational perspective view comprising a double ring having slits of the upper part and the lower part (the rings).

FIG. 21 shows an elevational perspective view comprising a double ring where 75 represents the slit of the upper part 72 and 76 represents the slit of the lower part 73. Both of the slits 75 and 76 have a substantially tongued course.

Figure 22:
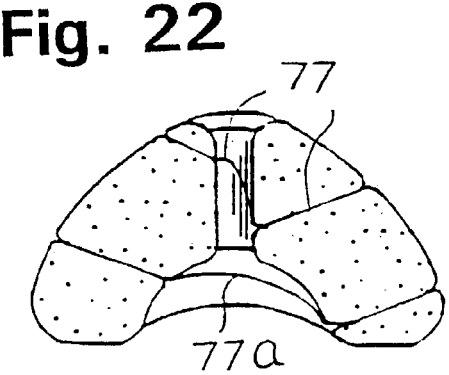
FIG. 22 shows a cross sectional perspective view of a curl-shaped embodiment of the device.

FIG. 22 shows a cross sectional perspective view of a curl-shaped embodiment of the device in which the slits 77 and 77a extend through the entire device and contribute to the curl-shape.

Figure 23:
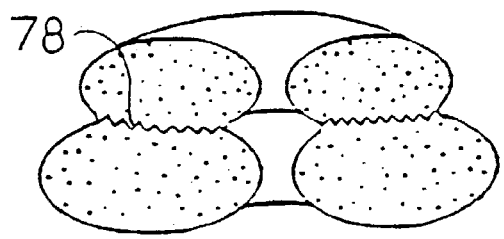
FIG. 23 shows a sectional perspective view of an embodiment of the device comprising curl-shaped element or a double ring.

FIG. 23 shows a sectional perspective view of a curl-shaped embodiment of the device or a double ring in which the surfaces of the ring elements which are in contact with each other have a surface pattern preventing the rings from sliding apart. In the embodiment shown, the pattern is represented by circular grooves which, as appears from the cross sectional view 78, fit into each other.

Figure 24:
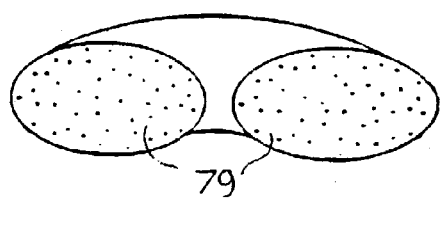
FIG. 24 shows a cross sectional perspective view of a ring-formed embodiment.

FIG. 24 shows a cross sectional perspective view of a ring-formed embodiment of the device in which the passage for the ligament is in the centre and in which the dimensions of the cross section areas of the ring 79 are substantially the same.

Figure 25:
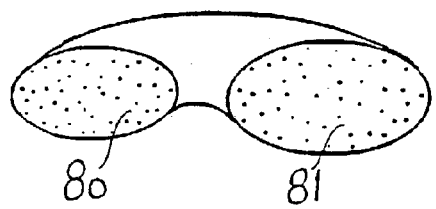
FIG. 25 shows a cross sectional perspective view of a ring-shaped element in which the hole or passage of the ring is placed eccentrically.

FIG. 25 shows a cross sectional perspective view of a ring-shaped element in which the hole or passage of the ring is placed eccentrically and in which one part of the ring in a cross section 81 differs in size from the corresponding part 80. The specific dimensions of such a ring-shaped embodiment of the device may be individually adapted in accordance with the anatomical conditions of the patient.

Figure 26:
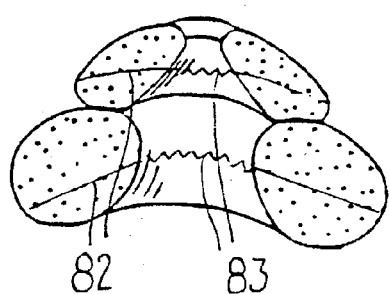
FIG. 26 shows a cross sectional perspective view of an embodiment of the device corresponding to the one seen in FIG. 16.

FIG. 26 shows a cross sectional perspective view of an embodiment of the device corresponding to the one seen in FIG. 16. However, in this embodiment the slit 82 extends through each of the ring-shaped elements and furthermore, the surfaces constituting the slit comprise grooves located in a substantially radial direction which thereby forms a substantially zigzag course at the surface of central passage for the ligament.

Figure 27:
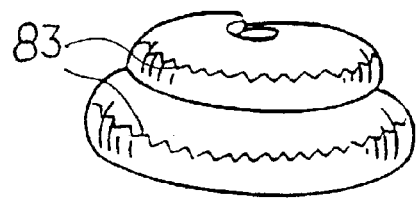
FIG. 27 shows a perspective view of an embodiment similar to the one shown in FIG. 26.

FIG. 27 shows a perspective view of an embodiment similar to the one shown in FIG. 26. The zigzag course of the slit 83, representing radially extending grooves which fit into each other, is clearly seen at the outer surface of each of the ring elements constituting the device. However, the grooves need not extend completely from the inner to the outer surface of the device but may be present in located areas only.

Figure 28:
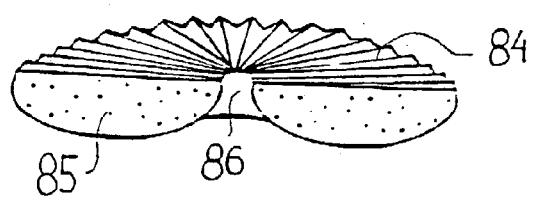
FIG. 28 shows a cross sectional perspective view of a ring-shaped element, e.g. corresponding to the lower part of the ring-shaped element seen in FIG. 27.

FIG. 28 shows a cross sectional perspective view of a ring-shaped element, e.g. corresponding to the lower part of the ring-shaped element seen in FIG. 27. The grooves 84 extend from the periphery into the centre 86 of the ring-shaped element 85.

Figure 29:
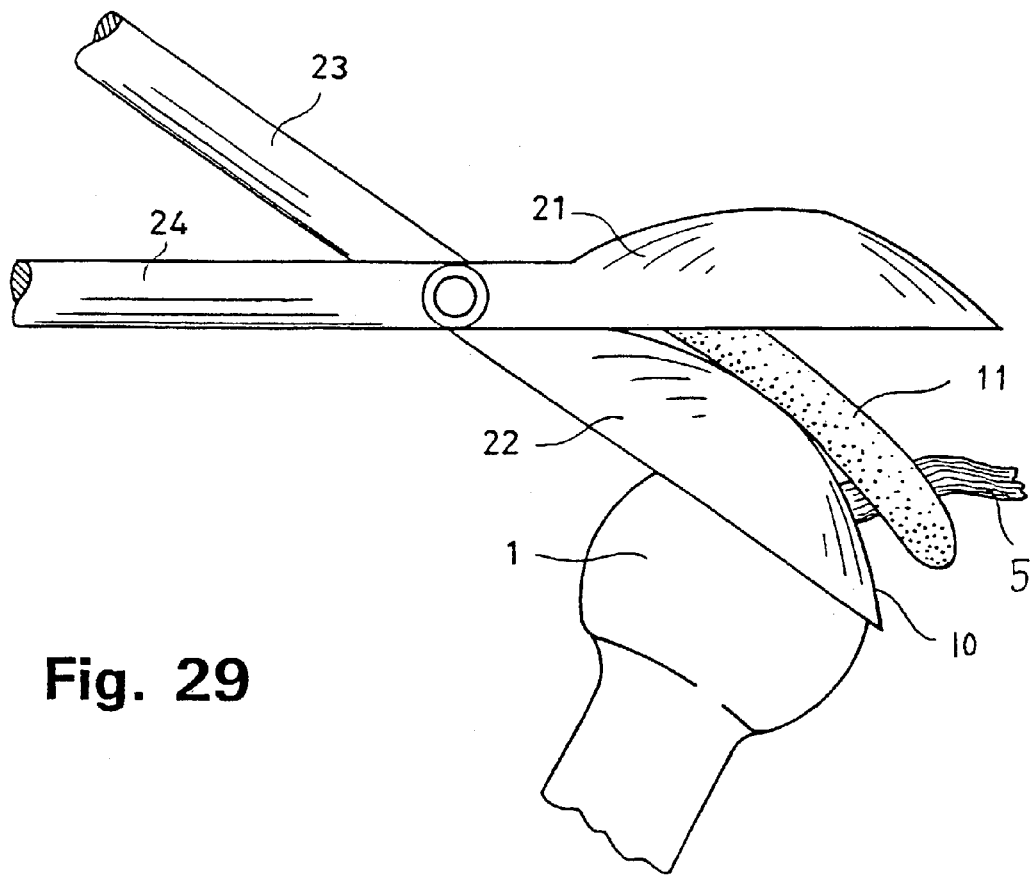
FIG. 29 shows a perspective view of one embodiment of an instrument with the prosthetic device located between the upper part of the instrument facing the surface corresponding to the acetabulum in situ and the lower part facing the femoral head.

FIG. 29 shows a perspective view of one embodiment of an instrument with the prosthetic device 11 located between the upper part 21 of the instrument facing the acetabulum (not shown) and the lower 22 part of the instrument having a concave shape facing the femoral head 1. The prosthetic device 11 is placed around the femoral ligament 5 when the upper 21 and lower 22 parts of the instrument are allowed to open by operating the handle 24 connected to the part 21 and the handle 23 connected to the part 22. As appears from the drawing, the handles 23 and 24 may be moved relatively to a common axis.

Figure 30:
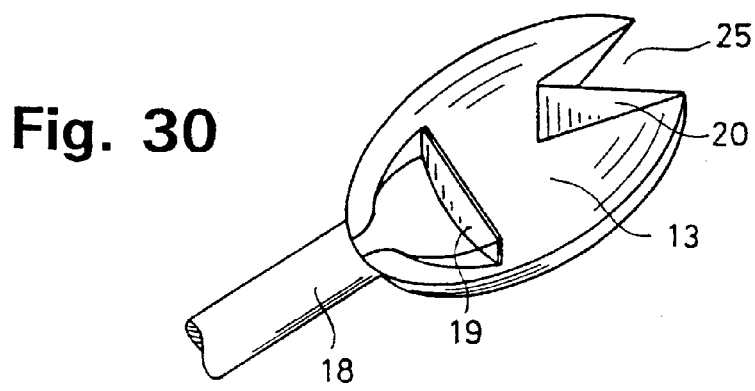
FIG. 30 shows a perspective view of the upper part of the instrument as shown in FIG. 29.

FIG. 30 shows a perspective view of the upper part of the instrument as shown as 21 in FIG. 29 with a view into the concave surface facing the convex surface of the lower part 22 shown in FIG. 29. Means for pushing 19 are shown which in one embodiment substantially have the shape of a stirrup where the base pushes the prosthetic device towards the means 20 for opening the slit of the prosthetic device. The means 20 comprises a V-shaped incision 25 having elevated edges forming a wedge which forces the slit of the prosthetic device to open when the prosthetic device is pushed towards the wedge by the base portion of the means 19. The slit of the prosthetic device is gradually widening while being pushed by 19 towards the means 20 whereby the prosthetic device can be placed around the ligament which is fixed within the incision 25 of the instrument. The incision 25 is shown as V-shaped, however any other shape allowing the ligament to be situated in the slit is within the scope of the invention. The means 20 encompass any embodiment suitable for placing the device around the ligament, accordingly, the means could include a spring which separates the mating surfaces of the slit. The upper part 21 in FIG. 29 of the instrument may also comprise two moveable parts which together substantially form a concave cavity mating the lower part of the instrument shown as 22 in FIG. 29. The movable parts may furthermore form an incision 25 by having parts separated from each other. In addition, the movable parts may be able to overlap and may comprise fastening means for the prosthetic device, e.g. for each side of the slit, so that when the movable parts are moved apart, the slit of the device is forced to open allowing the device to be placed around the ligament. In a still other embodiment, the inner surface of the upper part of the instrument 13 comprises means for opening the slit of the prosthetic device which is operated separately, e.g. in form of a string or wire connected to the device on each side of the slit so that the slit can be opened by pulling the string. A suitable direction of the pull can be secured, e.g. by fastening the string to a suitable point at the periphery of the concave cavity 13, e.g. by letting the string to pass through an eyelet. The means 19 as well as any string or wire may be operated by means extending through the handle 18.

Figure 31:
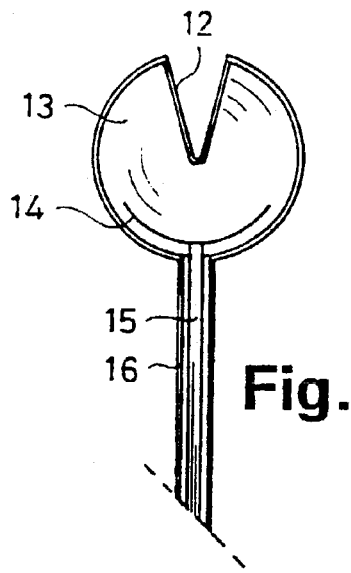
FIG. 31 shows a sectional perspective view of an embodiment of the upper part of the instrument comprising an edge or wall of a V-shaped incision.

FIG. 31 shows a sectional perspective view of an embodiment of the upper part of the instrument comprising an edge or wall of a V-shaped incision 12 of the inner surface 13. Pushing means 14 are connected to a handle 15 positioned within the handle 16 of the upper part of the instrument as also shown. The pushing means 14 have a base portion which is adapted to the shape of the prosthetic device.

Figure 32:
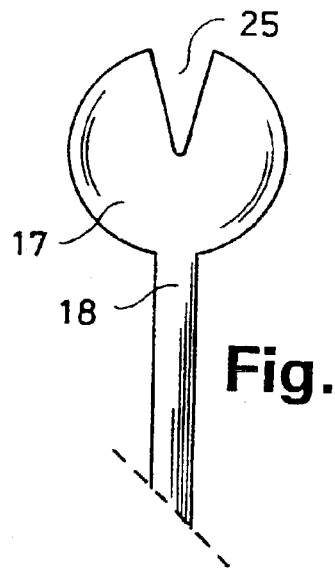
FIG. 32 shows a perspective view of the embodiment shown in FIG. 31 but seen from above.

FIG. 32 shows a perspective view of the embodiment shown in FIG. 31 but seen from above. The incision 25 enables the instrument to be placed in the joint without impeding the function or anchoring of ligamentum femoris as this is situated between the "legs" of the incision.

Figure 33:
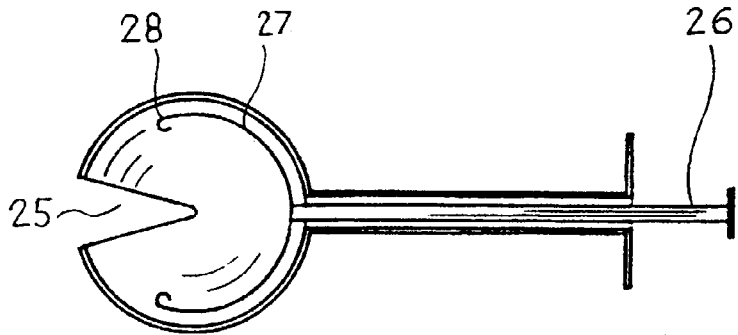
FIG. 33 shows a perspective view of an embodiment of the upper part of the instrument comprising pushing means and means for securing the prosthetic device.

FIG. 33 shows a perspective view of an embodiment of the upper part of the instrument in which the pushing means 27 comprise means 28 for securing the prosthetic device.

The means 28 have the shape of a hook located on each leg of the pushing means which are adapted to guide the prosthetic device. The prosthetic device is placed so that the outer or distal opening of the slit corresponds to the incision 25 of the instrument, the hook 28 on each side may then be secured to the device on the corresponding side of the slit. Preferably, in this position, the slit is open to receive the ligament. When the handle 26 is pushed towards the incision where the ligament is placed, the prosthetic device will be placed around the ligament, and the slit may then allow to close as the hook on each side (holding the device) let go when the pushing means are moved further on. As appears from FIG. 33, the pushing means may be operated by a part located within the outer handle of the upper part of the instrument which thereby functions as a guide.

Figure 34:
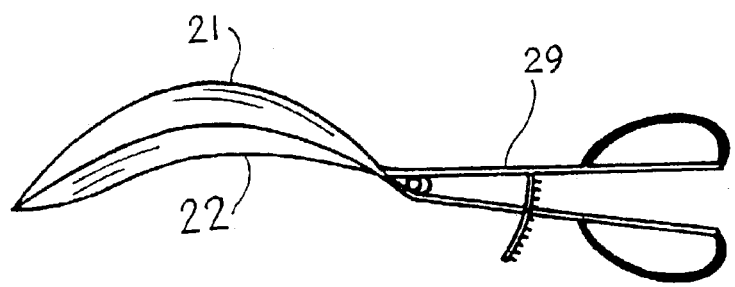
FIG. 34 shows a perspective view of a scissors-like embodiment of an instrument suitable or insertion of the device into the joint.

FIG. 34 shows a perspective view of a scissors-like embodiment of an instrument where 21 represents the upper part and 22 the lower part of the instrument. The prosthetic device is placed between those parts when inserted into the joint. Incisions as well as pushing means as described for the embodiments above may also be present.

Figure 35:
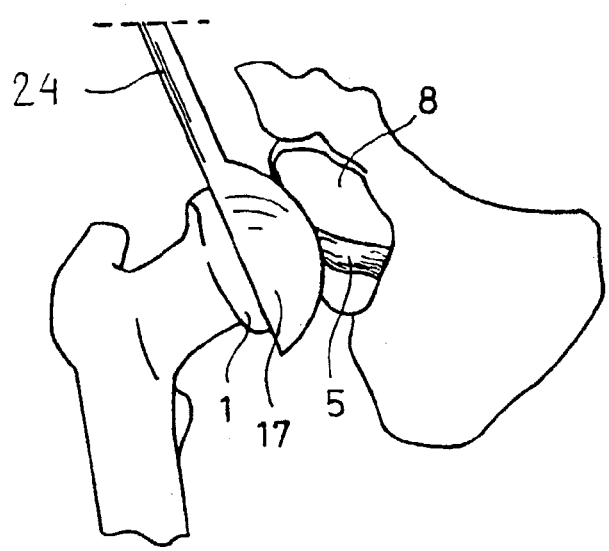
FIG. 35 shows a perspective elevational view of a hip joint wherein the femoral head has been retracted from the acetabulum giving space for the insertion of the device by use of an embodiment of the instrument according to the invention.

FIG. 35 shows a perspective elevational view of a hip joint. The femoral head 1 has been retracted from the acetabulum 8 giving a space in the joint of approximately 1-2 cm. The outer surface of the upper part of the instrument 17 having a handle 24 is placed on the femoral head 1. The lower part of the instrument (not seen) is present within the upper part 17, the ligament 5 is located in the corresponding incisions (not seen) of the lower and upper part 17 of the instrument.

Figure 36:
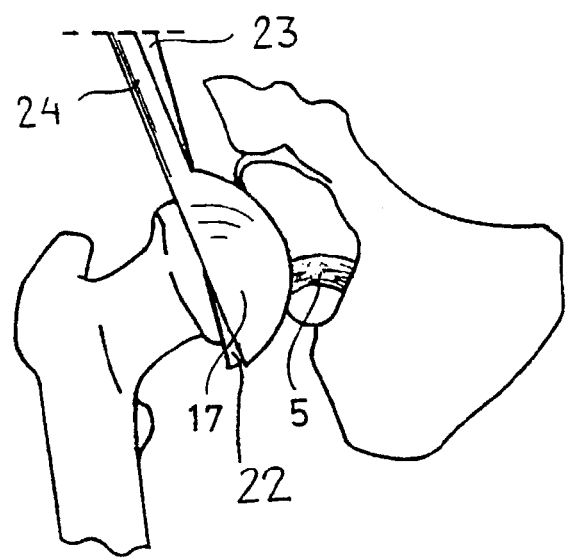
FIG. 36 shows a view similar to the one is FIG. 35 in which the insertion of the device is taken place. The upper and lower part of the instrument now gradually opened for delivering the device into the joint and to place the device around the ligament.

FIG. 36 shows a view similar to the one is FIG. 35 in which the handle 23 of the lower part of the instrument is now seen above the handle 24 of the upper part 17 of the instrument. The prosthetic device located between the upper and lower part 22 of the instrument may now be pushed towards the ligament 5 as the upper and lower part 22 of the instrument are now let open by operating the handles 23 and 24.

The invention claimed is:

1. A prosthetic device for insertion into a joint cavity of a joint of a vertebrate, said device consisting of a biocompatible material comprising at least a first polymeric component and a second polymeric component, wherein the chain length of the first polymeric component is longer than the chain length of the second polymeric component, said first and second polymeric components are not polytetrafluoroethylene or polyurethane, and wherein said first polymeric component has a carbon-backbone and the first polymeric component and the second polymeric component are compounded to form a bidispergent system.

2. The prosthetic device according to claim 1, wherein the first polymeric component is selected from the group consisting of polyacrylates, polystyrene, polyethers, polyvinylalcohol, polyethylene, and polypropylene.

3. The prosthetic device according to claim 2, wherein the first and the second polymeric component comprises the same monomeric component.

4. The prosthetic device according to claim 2, wherein the first polymeric component comprises a copolymer of polyethylene and polypropylene, and the second polymer is grafted to the first polymer.

5. The prosthetic device according to claim 4, wherein the second polymeric component is selected from the group consisting of polyethylene oxides, and polyvinylpyrrolidone.

6. The prosthetic device according to claim 1, wherein the second polymeric component is selected from the group consisting of polyacrylates, polystyrene, polyethers, polyvinylalcohol, polyethylene, and polypropylene.

7. The prosthetic device according to claim 6, wherein the second polymeric component is cross-linked.

8. A prosthetic device according to claim 7, wherein the cross-linking is achieved with radiation.

9. A prosthetic device according to claim 8, wherein the forms of radiation are selected from the group comprising high-energy electrons, gamma rays, photons, microwaves, and thermal radiation.

10. The prosthetic device according to claim 1, wherein the chain length of the first polymeric component is above 100 monomer units.

11. The prosthetic device according to claim 1, wherein the first polymeric component is a cross-linked polymer, and the second polymer is grafted to the first polymer.

12. A prosthetic device according to claim 11, wherein the body of the unit further comprises a slit extending from the surface of the body to the hole.

13. A prosthetic device according to claim 1, wherein said device is adapted to alleviate conditions associated with worn cartilage by providing a spacer function and/or to exert pressure distribution in the joint when the joint is loaded and/or to provide at least part of the sliding/rotating movement of the joint by internal movement of at least part of the device.

14. A prosthetic device according to claim 1, wherein the device is capable of locking itself to an intra-articular component and thereby being fixed or retained in the joint cavity in a manner which is substantially non-invasive with respect to cartilage and bone natively present in the joint cavity.

15. A prosthetic device according to claim 14, wherein the units are adapted not to interfere with intra-articular components when the device is in the joint cavity.

16. A prosthetic device according to claim 1, wherein the polymer material is obtained by cross-linking polyethylene, polypropylene or polyvinylpyrrolidone or combinations or co-polymers thereof.

17. A prosthetic device according to claim 1, wherein the polymer material meets mechanical properties in that the E modulus (Young's modulus) is at least 10 MPa.

18. A prosthetic device according to claim 1, wherein the device comprises more than one more unit.

19. A prosthetic device according to claim 1, wherein the polymer is subjected or further subjected to surface treatment to obtain optimized wetting ability and to obtain biocompatibility and resistance to heat treatment for sterilization.

20. A prosthetic device according to claim 1, which device, when present in situ, comprises at least one ring-shaped element.

21. A prosthetic device according to claim 20, wherein the ring-shaped element has a shape of a horseshoe, a torus, or a curl.

22. A prosthetic device according to claim 21, wherein the ring-shaped element has an upper convex shape and a lower concave shape.

23. A prosthetic device according to claim 1, for the articulation of a hip of a human, which device is adapted so that it, when present in situ in the human hip joint cavity, comprises at least one element surrounding ligamentum capitis femoris.

24. A prosthetic device according to claim 1, in which the element which is adapted to surround the ligament when present in situ, has such a shape and such properties that it can be placed around the ligament and, when placed around the ligament, will stay interlocked with the ligament.

25. A prosthetic device according to claim 1, which is a hip endoprothese and wherein the element has a shape and properties permitting arranging the element around ligamentum capitis femoris.

26. A prosthetic device according to claim 1, having such shape and/or properties that it is capable of replacing or supplementing worn or damaged cartilage in the joint and/or is capable of preventing wear of the native cartilage of the joint.

27. A prosthetic device according to claim 1, wherein the shape of the device mating the load bearing part of the joint is substantially circular.

28. A prosthetic device according to claim 27, wherein the diameter of the device in situ and when the joint is loaded is such that it substantially covers the surface area of the load bearing part of the joint which in the normal joint is covered with cartilage.

29. A prosthetic device according to claim 28, wherein the joint is the hip joint, and wherein the diameter of the device is such that the surface of caput femoris is substantially covered when the joint is loaded.

30. A prosthetic device according to claim 27, wherein diameter of the device is between 15-80 mm.

31. A prosthetic device according to claim 1, wherein the thickness of the device is between 2-60 mm.

32. A prosthetic device according to claim 1, wherein the device comprises parts overlapping each other.

33. A prosthetic device according to claim 32, wherein the overlapping parts, on their mating surfaces have an interlocking surface structure.

34. A prosthetic device according to claim 33, wherein the interlocking surface structures constitute grooves.

35. A prosthetic device according to claim 34, wherein the interlocking surface structures are grooved in a radial direction.

36. A prosthetic device according to claim 34, wherein the interlocking surface structures are grooved in a circular direction.

37. A prosthetic device according to claim 33, wherein the interlocking surface structures constitute elevations and corresponding depressions.

38. A prosthetic device according to claim 1, wherein the E modulus (Young's modulus) of the material of at least part of the device is at least 10 MPa.

39. A prosthetic device according to claim 1, wherein the material constituting the device comprises polypropylene.

40. A method of the prosthetic device according to claim 1, for establishing slidability and/or distributing pressure in a joint of a vertebrate by inserting into the joint cavity of the joint a prosthetic device, said device capable of locking itself to an intra-articular component and thereby being fixed or retained in the joint cavity in a manner which is substantially non-invasive with respect to cartilage and bone natively present in the joint cavity.

41. A method for establishing slidability and/or pressure distribution in a joint of a vertebrate comprising inserting into the joint cavity of the joint, the prosthetic device according to claim 1, which is capable of locking itself to an intra-articular component and thereby being fixed or retained in the joint cavity in a manner which is substantially non-invasive with respect to cartilage and bone natively present in the joint cavity.

42. A prosthetic device for insertion into a joint cavity of a joint of a vertebrate, said device consisting of a biocompatible material comprising at least a first polymeric component, a second polymeric component, and a third polymeric component, wherein the chain length of the first polymeric component is longer than the chain length of the second polymeric component, said first and second polymeric components are not polytetrafluoroethylene or polyurethane, and said third polymeric component being different from the first and/or the second polymeric component.

43. The prosthetic device according to claim 42, wherein the third polymeric component is selected from the group consisting of polyethylene oxides, and polyvinylpyrrolidone.

44. The prosthetic device according to claim 42, wherein the third polymeric component is grafted to the first and/or the second polymeric components.

45. A prosthetic device for insertion into a joint cavity of a joint of a vertebrate, said device having a body with a surface and a hole, and said device consisting of a biocompatible material comprising at least a first polymeric component and a second polymeric component, wherein the chain length of the first polymeric component is longer than the chain length of the second polymeric component, said first and second polymeric components are not polytetrafluoroethylene or polyurethane, and wherein the device further comprises a slit in the body of the device extending through the body of the device from the surface of the body to the hole.

46. A prosthetic device according to claim 45, wherein the device further comprises a means of enabling a passage through the body of the device to the hole.

47. A prosthetic device according to claim 45, wherein the body of the unit further comprises a hole extending through the body of the device.

48. A prosthetic device for insertion into a joint cavity of a joint of a vertebrate, said device consisting of a biocompatible material comprising at least a first polymeric component and a second polymeric component, wherein the chain length of the first polymeric component is longer than the chain length of the second polymeric component, said first and second polymeric components are not polytetrafluoroethylene or polyurethane, and said device is capable of locking itself to an intra-articular component by at least one element of the device surrounding the intra-articular component in such a manner that displacement of the element is limited by interlocking with said component.

49. A prosthetic device according to claim 48, wherein the element completely or substantially completely surrounds an intra-articular component being a ligament.

50. A prosthetic device according to claim 48, wherein the element, when present in situ, permits the ligament to extend through the element and substantially exert its natural function on the joint.

51. A prosthetic device according to claim 48, wherein the element surrounding the intra-articular component constitutes the device.

* * * * *